United States Patent
Kiesel et al.

(10) Patent No.: US 9,029,800 B2
(45) Date of Patent: May 12, 2015

(54) COMPACT ANALYZER WITH SPATIAL MODULATION AND MULTIPLE INTENSITY MODULATED EXCITATION SOURCES

(75) Inventors: Peter Kiesel, Palo Alto, CA (US); Joerg Martini, San Francisco, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 710 days.

(21) Appl. No.: 13/206,436

(22) Filed: Aug. 9, 2011

(65) Prior Publication Data

US 2013/0037726 A1    Feb. 14, 2013

(51) Int. Cl.
  *G01J 1/58*    (2006.01)
  *G01N 21/64*   (2006.01)
  *G01J 3/36*    (2006.01)
  G01N 21/05     (2006.01)
  G01N 21/65     (2006.01)
  (Continued)

(52) U.S. Cl.
  CPC . *G01J 3/36* (2013.01); *G01N 21/05* (2013.01); *G01N 21/6428* (2013.01); *G01N 21/65* (2013.01); *G01J 2003/104* (2013.01); *G01N 2021/6419* (2013.01); *G01N 2201/0691* (2013.01); *G01N 2015/145* (2013.01); *G01N 2015/1006* (2013.01); *G01N 15/1459* (2013.01)

(58) Field of Classification Search
  CPC .. G01J 3/36; G01J 2003/104; G01N 21/6428; G01N 15/1459; G01N 21/05; G01N 21/65; G01N 2021/6419; G01N 2201/0691; G01N 2015/145; G01N 2015/1006
  USPC ............ 250/383, 458.1, 459.1, 364; 356/314
  See application file for complete search history.

(56) References Cited

U.S. PATENT DOCUMENTS

| | | | |
|---|---|---|---|
| 2,708,389 A | 5/1955 | Kavanagh | |
| 3,357,230 A | 12/1967 | Topaz | |

(Continued)

FOREIGN PATENT DOCUMENTS

| | | |
|---|---|---|
| EP | 0354067 | 2/1990 |
| EP | 0442738 | 8/1991 |

(Continued)

OTHER PUBLICATIONS

U.S. Appl. No. 13/113,021, "Analyzers With Time Variation Based on Color-Coded Spatial Modulation", filed May 20, 2011.

(Continued)

*Primary Examiner* — David Porta
*Assistant Examiner* — Gisselle Gutierrez
(74) *Attorney, Agent, or Firm* — Hollingsworth Davis, LLC

(57) ABSTRACT

A compact analyzer includes a flow cell having a flow channel through which a sample is made to pass. First and second light sources are arranged to emit first and second excitation light into first and second overlapping portions of the flow channel, respectively. The first excitation light stimulates a first light emission from particles of a first particle type that may be present in the sample; the second excitation light stimulates a second light emission from particles of a second particle type. A detector receives the first and second light emission from the corresponding particles present in the sample in a detection portion of the flow channel, and provides a detector output based on the received light emission. The light sources are modulated at different frequencies so that a frequency analysis of the detector output can provide separate information about the first and second particle types.

18 Claims, 14 Drawing Sheets

(51) Int. Cl.
*G01J 3/10* (2006.01)
*G01N 15/14* (2006.01)
*G01N 15/10* (2006.01)

(56) References Cited

U.S. PATENT DOCUMENTS

| | | | |
|---|---|---|---|
| 3,797,911 A | 3/1974 | Kogelnik et al. | |
| 3,915,573 A | 10/1975 | Knoll et al. | |
| 3,958,252 A | 5/1976 | Kashio | |
| 3,973,118 A | 8/1976 | LaMontagne | |
| 4,081,277 A | 3/1978 | Brault et al. | |
| 4,131,899 A | 12/1978 | Christou | |
| 4,251,733 A | 2/1981 | Hirleman | |
| 4,427,296 A | 1/1984 | Demarest et al. | |
| 4,455,089 A | 6/1984 | Yeung et al. | |
| 4,514,257 A | 4/1985 | Karlsson et al. | |
| 4,536,762 A | 8/1985 | Moates | |
| 4,573,796 A | 3/1986 | Martin et al. | |
| 4,715,672 A | 12/1987 | Duguay et al. | |
| 4,730,922 A | 3/1988 | Bach et al. | |
| 4,764,670 A | 8/1988 | Pace et al. | |
| 4,793,705 A | 12/1988 | Shera | |
| 4,820,042 A | 4/1989 | Barger | |
| 4,822,998 A | 4/1989 | Yokota et al. | |
| 4,957,371 A | 9/1990 | Pellicori et al. | |
| 4,959,674 A | 9/1990 | Khuri-Yakub et al. | |
| 4,976,542 A | 12/1990 | Smith | |
| 5,028,545 A | 7/1991 | Soini | |
| 5,080,462 A | 1/1992 | Goto | |
| 5,144,498 A | 9/1992 | Vincent | |
| 5,151,585 A | 9/1992 | Siebert | |
| 5,159,199 A | 10/1992 | Labaw | |
| 5,166,755 A | 11/1992 | Gat | |
| 5,218,426 A | 6/1993 | Hall et al. | |
| 5,243,614 A | 9/1993 | Wakata et al. | |
| 5,254,919 A | 10/1993 | Bridges et al. | |
| 5,281,305 A | 1/1994 | Lee et al. | |
| 5,305,082 A | 4/1994 | Bret | |
| 5,312,535 A | 5/1994 | Waska et al. | |
| 5,324,401 A | 6/1994 | Yeung et al. | |
| 5,370,842 A | 12/1994 | Miyazaki et al. | |
| 5,394,244 A | 2/1995 | Tsai | |
| 5,410,404 A | 4/1995 | Kersey et al. | |
| 5,414,508 A | 5/1995 | Takahashi et al. | |
| 5,434,667 A | 7/1995 | Hutchins et al. | |
| 5,437,840 A | 8/1995 | King et al. | |
| 5,445,934 A | 8/1995 | Fodor et al. | |
| 5,491,347 A | 2/1996 | Allen et al. | |
| 5,528,045 A * | 6/1996 | Hoffman et al. | 250/458.1 |
| 5,572,328 A | 11/1996 | Fouckhardt et al. | |
| 5,608,517 A | 3/1997 | Munk | |
| 5,631,734 A | 5/1997 | Stern et al. | |
| 5,666,195 A | 9/1997 | Shultz et al. | |
| 5,674,698 A | 10/1997 | Zarling et al. | |
| 5,677,769 A | 10/1997 | Bendett | |
| 5,682,038 A | 10/1997 | Hoffman | |
| 5,745,308 A | 4/1998 | Spangenberg | |
| 5,760,900 A | 6/1998 | Ito et al. | |
| 5,777,329 A | 7/1998 | Westphal et al. | |
| 5,784,507 A | 7/1998 | Holm-Kennedy et al. | |
| 5,792,663 A | 8/1998 | Fry et al. | |
| 5,793,485 A | 8/1998 | Gourley | |
| 5,798,222 A | 8/1998 | Goix | |
| 5,801,831 A | 9/1998 | Sargoytchev | |
| 5,825,792 A | 10/1998 | Villeneuve et al. | |
| 5,864,641 A | 1/1999 | Murphy et al. | |
| 5,872,655 A | 2/1999 | Seddon et al. | |
| 5,876,674 A | 3/1999 | Dosoretz et al. | |
| 5,880,474 A | 3/1999 | Norton et al. | |
| 5,909,278 A | 6/1999 | Deka et al. | |
| 5,917,606 A | 6/1999 | Kaltenbach | |
| 5,933,233 A | 8/1999 | Gunther | |
| 5,945,676 A | 8/1999 | Khalil et al. | |
| 5,953,138 A | 9/1999 | Ellis | |
| 5,958,122 A | 9/1999 | Fukuda et al. | |
| 5,982,478 A | 11/1999 | Ainsworth et al. | |
| 5,982,534 A | 11/1999 | Pinkel et al. | |
| 6,040,578 A | 3/2000 | Malin et al. | |
| 6,049,727 A | 4/2000 | Crothall | |
| 6,066,243 A | 5/2000 | Anderson et al. | |
| 6,091,502 A | 7/2000 | Weigl et al. | |
| 6,108,463 A | 8/2000 | Herron et al. | |
| 6,116,718 A | 9/2000 | Peeters et al. | |
| 6,122,536 A | 9/2000 | Sun et al. | |
| 6,137,117 A | 10/2000 | Feldstein et al. | |
| 6,169,604 B1 | 1/2001 | Cao | |
| 6,187,592 B1 | 2/2001 | Gourley | |
| 6,192,168 B1 | 2/2001 | Feldstein et al. | |
| 6,216,022 B1 | 4/2001 | Tyrrell et al. | |
| 6,249,346 B1 | 6/2001 | Chen et al. | |
| 6,275,628 B1 | 8/2001 | Jones et al. | |
| 6,285,504 B1 | 9/2001 | Diemeer | |
| 6,295,130 B1 | 9/2001 | Sun et al. | |
| 6,306,933 B1 | 10/2001 | Eiger et al. | |
| 6,307,623 B1 | 10/2001 | Papuchon et al. | |
| 6,310,690 B1 | 10/2001 | Cao et al. | |
| 6,353,475 B1 | 3/2002 | Jensen et al. | |
| 6,399,405 B1 | 6/2002 | Chen et al. | |
| 6,405,073 B1 | 6/2002 | Crowley et al. | |
| 6,429,022 B1 | 8/2002 | Kunz et al. | |
| 6,438,397 B1 | 8/2002 | Bosquet et al. | |
| 6,459,080 B1 | 10/2002 | Yin et al. | |
| 6,468,702 B1 | 10/2002 | Yi et al. | |
| 6,483,959 B1 | 11/2002 | Singh et al. | |
| 6,490,034 B1 | 12/2002 | Woias et al. | |
| 6,505,775 B1 | 1/2003 | Gu et al. | |
| 6,514,460 B1 | 2/2003 | Fendrock | |
| 6,519,037 B2 | 2/2003 | Jung et al. | |
| 6,525,308 B1 | 2/2003 | Schmidt-Hattenberger | |
| 6,556,854 B1 * | 4/2003 | Sato et al. | 600/407 |
| 6,558,945 B1 | 5/2003 | Kao | |
| 6,577,780 B2 | 6/2003 | Lockhart | |
| 6,580,507 B2 | 6/2003 | Fry et al. | |
| 6,603,548 B2 | 8/2003 | Church et al. | |
| 6,608,679 B1 | 8/2003 | Chen et al. | |
| 6,628,390 B1 | 9/2003 | Johnson | |
| 6,630,999 B2 | 10/2003 | Shroder | |
| 6,639,679 B2 | 10/2003 | Frojdh | |
| 6,665,113 B2 | 12/2003 | Aso et al. | |
| 6,678,502 B1 | 1/2004 | Sugaya et al. | |
| 6,694,158 B2 | 2/2004 | Polak | |
| 6,697,542 B2 | 2/2004 | Platzman et al. | |
| 6,700,664 B1 | 3/2004 | Honda et al. | |
| 6,704,104 B2 | 3/2004 | Li | |
| 6,710,871 B1 | 3/2004 | Goix | |
| 6,736,484 B2 | 5/2004 | Nakamura | |
| 6,742,884 B2 | 6/2004 | Wong et al. | |
| 6,755,983 B2 | 6/2004 | Yudasaka | |
| 6,759,713 B2 | 7/2004 | Chabinyc et al. | |
| 6,768,555 B2 | 7/2004 | Chen et al. | |
| 6,781,690 B2 | 8/2004 | Armstrong et al. | |
| 6,785,002 B2 | 8/2004 | Zarrabian et al. | |
| 6,795,190 B1 | 9/2004 | Paul et al. | |
| 6,796,710 B2 | 9/2004 | Yates et al. | |
| 6,800,849 B2 | 10/2004 | Staats | |
| 6,806,925 B2 | 10/2004 | Gaudiana et al. | |
| 6,809,865 B2 | 10/2004 | Chen | |
| 6,815,125 B1 | 11/2004 | Okabe et al. | |
| 6,816,257 B2 | 11/2004 | Goix | |
| 6,830,856 B2 | 12/2004 | Tsai et al. | |
| 6,838,361 B2 | 1/2005 | Takeo | |
| 6,839,140 B1 | 1/2005 | O'Keefe et al. | |
| 6,856,718 B2 | 2/2005 | Kane et al. | |
| 6,865,198 B2 | 3/2005 | Taubman | |
| 6,867,420 B2 | 3/2005 | Mathies et al. | |
| 6,867,868 B1 | 3/2005 | Barbarossa | |
| 6,870,149 B2 | 3/2005 | Berezin | |
| 6,872,320 B2 | 3/2005 | Wong et al. | |
| 6,872,588 B2 | 3/2005 | Chabinyc et al. | |
| 6,887,713 B2 | 5/2005 | Nelson et al. | |
| 6,890,050 B2 | 5/2005 | Ready et al. | |
| 6,906,792 B2 | 6/2005 | Ortyn et al. | |
| 6,927,852 B2 | 8/2005 | Reel | |
| 6,934,435 B2 | 8/2005 | Kane | |

(56) References Cited

U.S. PATENT DOCUMENTS

| | | | |
|---|---|---|---|
| 6,952,603 B2 | 10/2005 | Gerber et al. |
| 6,972,261 B2 | 12/2005 | Wong et al. |
| 6,983,176 B2 | 1/2006 | Gardner et al. |
| 7,011,630 B2 | 3/2006 | Desai et al. |
| 7,024,236 B2 | 4/2006 | Ford et al. |
| 7,034,933 B2 | 4/2006 | Walker et al. |
| 7,046,357 B2 | 5/2006 | Weinberger et al. |
| 7,064,836 B2 | 6/2006 | Bechtel et al. |
| 7,106,441 B2 | 9/2006 | Sun et al. |
| 7,130,321 B2 | 10/2006 | Spinelli et al. |
| 7,136,161 B2 | 11/2006 | Nakamura |
| 7,149,396 B2 | 12/2006 | Schmidt et al. |
| 7,195,465 B2 | 3/2007 | Kane et al. |
| 7,195,797 B2 | 3/2007 | Mearini et al. |
| 7,248,361 B2 | 7/2007 | Kiesel et al. |
| 7,252,360 B2 | 8/2007 | Hersch et al. |
| 7,259,856 B2 | 8/2007 | Kachanov et al. |
| 7,268,868 B2 | 9/2007 | Kiesel et al. |
| 7,274,011 B2 | 9/2007 | Tennant et al. |
| 7,277,569 B2 | 10/2007 | Bruce et al. |
| 7,291,824 B2 | 11/2007 | Kiesel et al. |
| 7,305,112 B2 | 12/2007 | Curry et al. |
| 7,310,153 B2 | 12/2007 | Kiesel et al. |
| 7,315,667 B2 | 1/2008 | Schmidt et al. |
| 7,355,699 B2 | 4/2008 | Gilbert et al. |
| 7,358,476 B2 | 4/2008 | Kiesel et al. |
| 7,365,022 B2 | 4/2008 | Wong et al. |
| 7,372,435 B2 | 5/2008 | Kim |
| 7,386,199 B2 | 6/2008 | Schmidt et al. |
| 7,387,892 B2 | 6/2008 | Kiesel et al. |
| 7,391,517 B2 | 6/2008 | Trebbia et al. |
| 7,420,677 B2 | 9/2008 | Schmidt et al. |
| 7,433,552 B2 | 10/2008 | Kiesel et al. |
| 7,440,101 B2 | 10/2008 | Auer et al. |
| 7,456,953 B2 | 11/2008 | Schmidt et al. |
| 7,466,307 B2 | 12/2008 | Trent, Jr. |
| 7,466,409 B2 | 12/2008 | Scherer et al. |
| 7,471,399 B2 | 12/2008 | Kiesel et al. |
| 7,479,625 B2 | 1/2009 | Kiesel et al. |
| 7,479,652 B2 | 1/2009 | Greentree et al. |
| 7,496,463 B2 | 2/2009 | Nicoli et al. |
| 7,502,123 B2 | 3/2009 | Schmidt et al. |
| 7,506,268 B2 | 3/2009 | Jennings |
| 7,521,769 B2 | 4/2009 | Cunningham |
| 7,522,786 B2 | 4/2009 | Kiesel et al. |
| 7,529,438 B2 | 5/2009 | Schmidt et al. |
| 7,545,513 B2 | 6/2009 | Kiesel et al. |
| 7,547,904 B2 | 6/2009 | Schmidt et al. |
| 7,554,673 B2 | 6/2009 | Kiesel et al. |
| 7,633,629 B2 | 12/2009 | Kiesel et al. |
| 7,641,777 B2 | 1/2010 | Joseph et al. |
| 7,694,231 B2 | 4/2010 | Kocienda |
| 7,701,580 B2 | 4/2010 | Bassler et al. |
| 7,718,948 B2 | 5/2010 | Kiesel |
| 7,763,856 B2 | 7/2010 | Kiesel et al. |
| 7,817,254 B2 | 10/2010 | Hegyi et al. |
| 7,817,276 B2 | 10/2010 | Kiesel et al. |
| 7,830,517 B2 | 11/2010 | Beck et al. |
| 7,839,450 B2 | 11/2010 | Hing |
| 7,879,390 B2 | 2/2011 | Salleo et al. |
| 7,894,068 B2 | 2/2011 | Bassler et al. |
| 8,223,127 B2 | 7/2012 | Park |
| 8,629,981 B2 | 1/2014 | Martini et al. |
| 2002/0155485 A1 | 10/2002 | Kao |
| 2003/0000835 A1 | 1/2003 | Witt et al. |
| 2003/0020915 A1 | 1/2003 | Schueller et al. |
| 2003/0077660 A1 | 4/2003 | Pien et al. |
| 2003/0137672 A1 | 7/2003 | Moriya et al. |
| 2003/0161024 A1 | 8/2003 | Zhang et al. |
| 2003/0169311 A1 | 9/2003 | Kong Leong et al. |
| 2003/0178555 A1 | 9/2003 | Fang |
| 2003/0189711 A1 | 10/2003 | Orr et al. |
| 2003/0191377 A1 | 10/2003 | Robinson et al. |
| 2003/0197754 A1 | 10/2003 | Nakamura |
| 2003/0231272 A1 | 12/2003 | Nakamura et al. |
| 2003/0235924 A1 | 12/2003 | Adams et al. |
| 2004/0031684 A1 | 2/2004 | Witt |
| 2004/0038386 A1 | 2/2004 | Zesch et al. |
| 2004/0057050 A1 | 3/2004 | Beck et al. |
| 2004/0067167 A1 | 4/2004 | Zhang et al. |
| 2004/0109659 A1 | 6/2004 | Aylward et al. |
| 2004/0110099 A1 | 6/2004 | Kozawa et al. |
| 2004/0132214 A1 | 7/2004 | Lin et al. |
| 2004/0141884 A1 | 7/2004 | Unno et al. |
| 2004/0175734 A1 | 9/2004 | Stahler et al. |
| 2004/0178523 A1 | 9/2004 | Kim et al. |
| 2004/0223881 A1 | 11/2004 | Cunningham et al. |
| 2004/0228375 A1 | 11/2004 | Ghosh et al. |
| 2004/0252109 A1 | 12/2004 | Trent |
| 2004/0253835 A1 | 12/2004 | Kawase |
| 2005/0042615 A1 | 2/2005 | Smith et al. |
| 2005/0046821 A1 | 3/2005 | Hanson et al. |
| 2005/0068526 A1 | 3/2005 | Avrutsky |
| 2005/0099624 A1 | 5/2005 | Staehr et al. |
| 2005/0128479 A1 | 6/2005 | Gilbert et al. |
| 2005/0136358 A1 | 6/2005 | Paul et al. |
| 2005/0158868 A1 | 7/2005 | Trebbia et al. |
| 2005/0162650 A1 | 7/2005 | Yamamoto |
| 2005/0164320 A1 | 7/2005 | McDevitt et al. |
| 2005/0213082 A1 | 9/2005 | DiBernardo et al. |
| 2005/0255392 A1 | 11/2005 | Tsai et al. |
| 2006/0115749 A1 | 6/2006 | Toyoda |
| 2006/0121555 A1 | 6/2006 | Lean |
| 2006/0182659 A1 | 8/2006 | Unlu et al. |
| 2006/0193550 A1 | 8/2006 | Wawro et al. |
| 2006/0203224 A1 | 9/2006 | Sebastian et al. |
| 2006/0268260 A1 | 11/2006 | Liu et al. |
| 2007/0046301 A1 | 3/2007 | Kasapi |
| 2007/0070347 A1 | 3/2007 | Scherer et al. |
| 2007/0076210 A1 | 4/2007 | Kiesel et al. |
| 2007/0096039 A1* | 5/2007 | Kapoor et al. ............. 250/458.1 |
| 2007/0116609 A1 | 5/2007 | Baeuerle et al. |
| 2007/0145249 A1 | 6/2007 | Kiesel et al. |
| 2007/0165225 A1 | 7/2007 | Trainer |
| 2007/0166725 A1 | 7/2007 | McBride et al. |
| 2007/0186791 A1 | 8/2007 | Kim et al. |
| 2007/0201025 A1 | 8/2007 | Greenwald |
| 2008/0013092 A1 | 1/2008 | Matezos et al. |
| 2008/0095985 A1 | 4/2008 | Frey et al. |
| 2008/0179541 A1* | 7/2008 | LeBoeuf et al. ........... 250/459.1 |
| 2008/0181827 A1* | 7/2008 | Bassler et al. ................ 422/119 |
| 2008/0183418 A1 | 7/2008 | Bassler et al. |
| 2008/0186483 A1 | 8/2008 | Kiesel et al. |
| 2008/0186494 A1 | 8/2008 | Kiesel et al. |
| 2008/0186500 A1 | 8/2008 | Kiesel et al. |
| 2008/0187011 A1 | 8/2008 | Kiesel et al. |
| 2008/0213915 A1* | 9/2008 | Durack et al. ................ 436/172 |
| 2008/0299327 A1 | 12/2008 | Salleo et al. |
| 2009/0016690 A1 | 1/2009 | Schmidt et al. |
| 2009/0108214 A1* | 4/2009 | Shinoda et al. ............ 250/492.1 |
| 2009/0190121 A1 | 7/2009 | Hegyi et al. |
| 2009/0194705 A1 | 8/2009 | Kiesel et al. |
| 2009/0195773 A1 | 8/2009 | Bassler et al. |
| 2009/0195852 A1 | 8/2009 | Bassler et al. |
| 2009/0220189 A1 | 9/2009 | Kiesel et al. |
| 2010/0108910 A1* | 5/2010 | Morrell et al. ............. 250/459.1 |
| 2010/0155572 A1 | 6/2010 | Kiesel et al. |
| 2010/0155577 A1 | 6/2010 | Kiesel et al. |
| 2010/0157291 A1 | 6/2010 | Kiesel et al. |
| 2010/0201988 A1 | 8/2010 | Kiesel et al. |
| 2010/0256943 A1* | 10/2010 | Donnenberg et al. ......... 702/104 |
| 2011/0118571 A1* | 5/2011 | Mandelis et al. ............. 600/316 |
| 2013/0200277 A1* | 8/2013 | Li et al. ...................... 250/459.1 |
| 2014/0370612 A1 | 12/2014 | Kiesel et al. |

FOREIGN PATENT DOCUMENTS

| | | |
|---|---|---|
| EP | 0678881 | 11/1995 |
| EP | 1324018 | 7/2003 |
| EP | 1653217 | 6/2007 |
| EP | 1800752 | 6/2007 |
| EP | 1801553 | 6/2007 |
| EP | 1801562 | 6/2007 |
| EP | 1801564 | 6/2007 |

(56) References Cited

FOREIGN PATENT DOCUMENTS

| | | |
|---|---|---|
| EP | 1950552 | 7/2008 |
| JP | 02049143 | 2/1990 |
| JP | 02245638 | 10/1990 |
| JP | 03020642 | 1/1991 |
| JP | 04223261 | 8/1992 |
| JP | 04297888 | 10/1992 |
| JP | 05240774 | 9/1993 |
| JP | 06018421 | 1/1994 |
| JP | 08261922 | 10/1996 |
| JP | 2004252214 | 9/2004 |
| JP | 2005165073 | 6/2005 |
| JP | 2007518991 | 6/2005 |
| WO | WO95/20144 | 7/1995 |
| WO | WO9944042 | 9/1999 |
| WO | WO99/54730 | 10/1999 |
| WO | WO0039573 | 7/2000 |
| WO | WO00/62050 | 10/2000 |
| WO | WO0225269 | 3/2002 |
| WO | WO2004/033059 | 4/2004 |
| WO | WO2004063681 | 7/2004 |
| WO | WO2004/083820 | 9/2004 |
| WO | WO2005017498 | 2/2005 |
| WO | WO2005068971 | 7/2005 |
| WO | WO2005/108963 | 11/2005 |
| WO | WO2006/133360 | 12/2006 |
| WO | WO2007069840 | 6/2007 |

OTHER PUBLICATIONS

U.S. Application 13/206,439, "Particle Analyzer With Spatial Modulation and Long Lifetime Bioprobes", filed on even date herewith.
Kiesel et al., "'Spatially modulated emission' advances point-of-care diagnostics", Laser Focus World, Nov. 2010, pp. 47-50.
"Flow Cytometry", printed from www.wellscenter.iupui.edu/MMIA on Jan. 29, 2008, 4 pages.
"Optical Chopper—SR540—Optical Chopper System", Stanford Research Systems, Oct. 2008, 2 pages.
Adams et al., "Microfluidic Integration on Detector Arrays for Absorption and Fluorescence Micro-spectrometer", Sensors and Actuators, 2003, pp. 25-31.
Agilent Technologies, "Agilent 83453B High-Resolution Spectrometer—Technical Specifications", Feb. 2005, pp. 1-8.
Agilent Technologies "Developing Technology: HPLC-Chip/MS", May 25, 2011, 2 pages.
Bassler et al., "Class Identification of Bio-Molecules Based on Multicolor Native Fluorescence Spectroscopy", International Journal of High Speed Electronics and Systems, vol. 17, Issue 4, 2007, pp. 671-680.
Becker et al., "Polymer Microfabrication Methods for Microfluidic Analytical Applications", Electrophoresis, vol. 21, 2000, pp. 12-26. (abstract only).
Bernini et al., "Silicon Micromachined Hollow Optical Waveguides for Sensing applications", IEEE Journal on Selected Topics in Quantum Electronics, vol. 8, No. 1, Jan./Feb. 2002, pp. 106-110. (abstract only).
Bese et al., "A compact, affordable and portable CD4 T-cell machine", Int. Conf. AIDS 2002, Jul. 7-12, 2002, 1 pg.
Bhatta et al., "Rapid Identification of Microorganisms by Intrinsic Fluorescence", Proc. of SPIE, vol. 5699, 2005, pp. 9-18.
Cheung et al., "Impedance Spectroscopy Flow Cytometry: On-Chip Label-Free Cell Differentiation", Cytometry Part A, vol. 65A, 2005, pp. 124-132.
Cunningham et al., "Label-Free Assays on the Bind System", Journal of Biomolecular Screening, vol. 9, No. 6, 2004, pp. 481-490.
Devasenathipathy et al., "3 Electrokinetic Flow Diagnostics", in Breuer K.S. Ed. Micro-and Nano-Scale Diagnostic Techniques, Springer Verlag, New York, 2003, pp. 121-166.
Fuhr, Measuring with Light, Sensors Magazine Online, May 2000, 11 pages.
Fuji-Keizai USA, "Biosensor Market, R&D and Commercial Implication", 2004, 5 pages.

Goddard et al., Anti-Resonant Reflecting Optical Waveguides (ARROW), as Optimal Optical Detectors for MicroTAS Applications, dias.umist.ac.uk, 5 pages.
Henry et al., "Wavelength Response of Thin-Film Optical Position-Sensitive Detectors", J. Opt. A: Pure Appl. Opt., Vole. 4, 2002, pp. 527-534. (abstract only).
Hoffman, R. A., "Flow Cytometry: Instrumentation, Applications, Future Trends and Limitations", Springer Series on Fluorescence, vol. 6, 2008, pp. 307-342.
Holmes et al., "Label-Free Differential Leukocyte Counts Using a Microfabricated, Single-Cell Impedance Spectrometer", Sensors, 2007 IEEE, pp. 1452-1455. (abstract only).
Imade et al., "Comparison of a New, Affordable Flow Cytometric Method and the Manual Magnetic Bead Technique for CD4 T-Lymphocyte Counting in a Northern Nigerian Setting", Clinical and Diagnostic Laboratory Imm., Jan. 2005, p. 224-227.
Janossy et al., "Affordable CD4+-T-Cell Counting by Flow Cytometry:CD45 gating for Volumetric Analysis", Clinical and Diagnostic Laboratory Immunology, Sep. 2002, p. 1085-1094.
Johnson et al., "Introductions to Photonic Crystals: Bloch's Theorem, Band Diagrams, and Gaps (But No Defects)", Feb. 3, 2003, 16 pages.
Johnson, "Photonic Crystals: Periodic Surprises in Electromagnetism", printed from ab-initio.mit.edu on Oct. 5, 2006, 3 pages.
Jones et al., "Dielectrophoretic Liquid Actuation Nanodroplet Formation", Journal of Applied Physics, vol. 89, No. 2, 2001, pp. 1441-1448. (abstract only).
Kiesel et al., "Spatially Modulated Emission Advances Point-of-Care Diagnostics", Laser Focus World, Nov. 2010, pp. 47-50.
Kiesel et al., "Hand-held flow cytometer for point of care CD4 testing", APS March Meeting 2010, vol. 55, No. 2, 3 pages.
Konsziela, "Accurately Measure Laser Spectral Characteristics", 2006, 5 pages.
Kim et al., "Polymer-Planar-Lightwave-Circuit-Type Variable Optical Attenuator Fabricated by Hot Embossing Process" ETRI Journal, vol. 27, No. 1, Feb. 2004, pp. 10-16.
Law et al., "Low-Voltage Superlattice Asymmetric Fabry-Perot Reflection Modulator", IEEE Phot. Tech. Lett, vol. 3, No. 4, Apr. 1991, pp. 324-326. (abstract only).
Liang et al., "Refractive Index Measurement of Single Living Cell Using a Biophotonic Chip for Cancer Diagnosis Applications", 9th International Conference on Miniaturized Systems for Chemistry and Life Sciences, Oct. 2005, 3 pages.
Liu et al., "Nanowell Surface Enhanced Raman Scattering Arrays Fabricated by Soft-Lithography for Label-Free Biomolecular Detections in Integrated Microfluidics", Applied Physics Letters, vol. 87, 2005, pp. 1-3.
McNichols et al., "Optical Glucose Sensing in Biological Fluids: An Overview", Journal of Biomedical Optics, vol. 5, No. 1, Jan. 2000, pp. 5-16. (abstract only).
Murata, "Spectral Images Camera Using Linear Variable Interference Filter", Oct. 2003, 6 pages.
Schaefer et al., "Accuracy of Position Detection Using a Position-Sensitive Detector", IEEE Transactions on Instrumentation and Measurement, vol. 47, No. 4, Aug. 1998, pp. 914-919. (abstract only).
Schmidt et al., "Guiding Light in Fluids", applied Physics Letters, vol. 88, 2006, pp. 151109-1-1151109-3.
Schmidt et al., "Enhanced light-target interaction using a novel anti-resonant waveguide concept", SPIE Proc. 6094, 2006, pp. 80-89.
Schmidt et al., "Fluorescence Spectrometer-on-a-fluidic-chip", Lab Chop, 2007.
Seamer et al., "Sheath Fluid control to Permit Stable Flow in Rapid Mix Flow Cytometry", Cytometry, vol. 5699, 2005, pp. 75-79.
Sims et al., "Analysis of Single Mammalian Cells On-Chip", Lab Chip., vol. 7, Issue 4, Apr. 2007, pp. 423-440. (Abstract only).
Singh et al., "Analysis of cellular Structure by Light Scattering Measurements in a New Cytometer Design Based on a Liquid-Core Waveguide", IEEE Proceedings Nanobiotechnology, vol. 151, No. 1, Feb. 2004, pp. 10-16.
Singh et al., "Leaky ARROW Waveguides for Optical Chemical and Biosensors", 1998.

(56) References Cited

OTHER PUBLICATIONS

Spear et al., "Low noise position sensitive detector for optical probe beam deflection measurements", Rev. Sci. Instrum., vol. 67, No. 7, Jul. 1996, pp. 2481-2484. (abstract only).
SRU Biosystems, Inc., "BIND Biosensor TM Technology", Apr. 3, 2004 excerpt, 1 page.
Udd, "Good Sense", SPIE's OEMagazine, Aug. 2002, pp. 27-29.
Vogel, "Tunable Liquid Crystal Fabry-Perot Filters", Institute for Electrical and Optical Communication Engineering, University of Stuttgart, 2002, 10 pages. (abstract only).
Vollmer et al., "Multiplexed DNA Quantification by Spectroscopic Shift of Two Microsphere Cavities", Biophysical Journal, vol. 85, Sep. 2005, pp. 106.
Weismann et al., "Singlemode polymer waveguides for optical backplanes", Electronics Letters, vol. 32, No. 25, Dec. 5, 1996, pp. 2329-2330. (abstract only).
Dec. 19, 2012, File History for U.S. Appl. No. 11/315,992.
Oct. 24, 2012, File History for U.S. Appl. No. 12/024,490.
Oct. 24, 2012, File History for U.S. Appl. No. 12/025,394.
Jun. 27, 2013, File History for U.S. Appl. No. 12/098,584.
Oct. 22, 2014, File History for U.S. Appl. No. 14/474,742.
Oct. 22, 2014, File History for U.S. Appl. No. 14/155,094.
Oct. 22, 2014, File History for U.S. Appl. No. 11/698,338.
Oct. 22, 2014, File History for U.S. Appl. No. 13/113,021.
Oct. 22, 2014, File History for U.S. Appl. No. 11/698,409.
File History for EP Application No. 06126524.5 as retrieved from the European Patent Office electronic file system on Dec. 19, 2012, 140 pages.
File History for EP Application No. 09151643.5 as retrieved from the European Patent Office electronic file system on Jun. 27, 2013, 138 pages.
File History for EP Application No. 08150482.1 as retrieved from the European Patent Office electronic file system on Jun. 27, 2013, 82 pages.
File History for EP Application No. 09151644.3 as retrieved from the European Patent Office electronic file system on Oct. 22, 2014, 119 pages.
Jan. 22, 2015, File History for U.S. Appl. No. 11/698,338.

\* cited by examiner

COMPACT ANALYZER WITH SPATIAL MODULATION AND MULTIPLE INTENSITY MODULATED EXCITATION SOURCES

TECHNICAL FIELD

This application relates generally to techniques for performing sample analysis by exposing the sample to electromagnetic radiation and by evaluating electromagnetic radiation emitted by the sample. The application also relates to components, devices, systems, and methods pertaining to such techniques.

BACKGROUND

Various techniques have been proposed for performing sample analysis using light emanating from objects. For example, U.S. Pat. No. 7,358,476 (Kiesel et al.) discusses a fluidic structure with a channel along which is a series of sensing components to obtain information about objects traveling within the channel, such as droplets or other objects carried by a fluid. A sensing component includes a set of cells that photosense a range of photon energies that emanate from objects. A processor receives information about objects from the sensing components and uses it to obtain spectral information. Additional techniques are described, for example, in U.S. Patent Application Publications 2008/0181827 (Bassler et al.), 2008/0183418 (Bassler et al.), 2009/0195773 (Bassler et al.), 2009/0195852 (Bassler et al.), and 2010/0201988 (Kiesel et al.).

Also, various flow cytometry techniques have been proposed.

BRIEF SUMMARY

We have developed a new family of sample analysis devices, and related components, systems, and methods, that involve illuminating a sample with light from multiple light sources and detecting light that emanates from the illuminated sample. Typically, the sample comprises, or is suspected to comprise, particles of different particle types. The multiple light sources are designed to preferentially excite (including, broadly, any suitable interaction with) a particular one or ones of the particle types in favor of other particle types. For example, one light source may emit light at a wavelength that is effective to excite one particle type, and another light source may emit light at a different wavelength effective to excite a different particle type. The light sources are modulated at different frequencies, such that light emanates from the different particle types at the different modulation frequencies. The light emanating from the various particle types can be collected (in some embodiments) by a single detector, and a time-based (e.g. frequency) analysis of the detector output can provide separate information about the various particle types present in the sample. Some embodiments may also include a spatial filter, e.g. in the form of a mask that has a pattern of variable transmission. Relative motion between the particle(s) and the mask can provide additional modulation of the emanating light that falls on the detector, and thus additional modulation or fluctuation of the detector output. This additional modulation can be used to extract still more information from the detector output, such as speed, position, intensity, and/or size of individual particles. If desired, the disclosed techniques can be practiced in compact analyzers of robust design, suitable for use in point-of-care (POC) testing.

We therefore disclose herein, among other things, compact analyzers that include a flow cell having a flow channel through which a sample can be made to pass. First and second light sources may be arranged to emit first and second excitation light into first and second excitation portions of the flow channel, respectively. The first and second excitation portions may be partially overlapping, or they may be substantially completely overlapping. The first excitation light stimulates a first light emission from particles of a first particle type that may be present in the sample, and the second excitation light stimulates a second light emission from particles of a second particle type that may likewise be present in the sample. A detector may receive the first and second light emission from the corresponding particles present in the sample in a detection portion of the flow channel, the detection portion overlapping with the first and second excitation portions of the flow channel, the detector providing an output based on the received light emission. The light sources may be modulated at different frequencies so that a time-based (e.g. frequency) analysis of the detector output can provide separate information about the first and second particle types.

We also describe apparatuses for analyzing samples that may comprise particles of at least a first and second particle type. Such apparatuses may include a flow channel, a first and second light source, and a detector. The flow channel is configured to allow the sample to pass through it. The first light source is adapted to emit first excitation light into a first excitation portion of the flow channel, the first excitation light being adapted to stimulate a first light emission from particles of the first particle type. The second light source is adapted to emit second excitation light into a second excitation portion of the flow channel, the second excitation light being adapted to stimulate a second light emission from particles of the second particle type. The detector is disposed to receive the first and second light emission from the corresponding particles that may be present in the sample in a detection portion of the flow channel, the detection portion overlapping with the first and second portions of the flow channel. The detector provides a detector output based on the received light emission. The first light source emits the first excitation light at a first modulation frequency $v1$, and the second light source emits the second excitation light at a second modulation frequency $v2$ different from $v1$.

Such apparatuses may also include a spatial filter having a pattern of variable transmission, and the spatial filter may be disposed between the detection portion of the flow channel and the detector. The spatial filter may transmit light emanating from the particles that may be present in the flow channel by varying amounts as such particles travel along the detection portion of the flow channel. In some cases, the first and second modulation frequencies are each faster than a modulation associated with the variable transmission of the spatial filter, the latter modulation being proportional to a spatial frequency of the spatial filter and to the speed of a given particle through the flow channel. In some cases, the first and second excitation portions of the flow channel substantially overlap with each other and with the detection portion of the flow channel, and the spatial filter may span the detection portion.

In some cases, the apparatus also includes a controller coupled to the first and second light sources, and the controller may drive or modulate the first and second light sources at the different first and second modulation frequencies respectively.

In some cases, the first excitation light may have a first peak wavelength, and the second excitation light may have a second peak wavelength different from the first peak wavelength.

The first excitation light may be adapted to stimulate little or no light emission from particles of the second type, and the second excitation light may be adapted to stimulate little or no light emission from particles of the first type.

In some cases, the first light emission may be or include fluorescence emitted by particles of the first particle type when exposed to the first excitation light. The apparatus may also include an optical filter disposed between the detector and the flow channel, the optical filter adapted to preferentially transmit the first light emission and to preferentially block the first excitation light. The second light emission may also be or include fluorescence emitted by particles of the second particle type when exposed to the second excitation light, and the optical filter may also preferentially transmit the second light emission and preferentially block the second excitation light.

The apparatus may also include a signal processing unit coupled to the detector to receive the detector output. The signal processing unit may then provide a system output based on the detector output, the system output providing a first measure of the particles of the first particle type in the sample and a second measure of the particles of the second particle type in the sample.

We also disclose apparatuses for analyzing samples that may include particles of at least a first and second particle type, where the apparatuses may include a flow channel, a first and second light source, a detector, an optical filter, a spatial filter, a controller, and a signal processing unit. The first light source may emit first excitation light into a first excitation portion of the flow channel, and the first excitation light may be effective to stimulate a first light emission from particles of the first particle type and to stimulate little or no light emission from particles of the second type. The second light source may emit second excitation light into a second excitation portion of the flow channel, and the second excitation light may be effective to stimulate a second light emission from particles of the second particle type and to stimulate little or no light emission from particles of the first type. The detector, which may be only one detector having only one output signal, may be disposed to receive the first and second light emission from the corresponding particles that may be present in the sample in a detection portion of the flow channel, the detection portion overlapping with the first and second portions of the flow channel, the detector providing a detector output based on the received light emission. The optical filter may be disposed between the detector and the flow channel, and it may preferentially transmit the first and second light emission and preferentially block the first and second excitation light. The spatial filter may have a pattern of variable transmission, and may be disposed between the detection portion of the flow channel and the detector. The spatial filter may also be adapted to transmit light emanating from the particles that may be present in the flow channel by varying amounts as such particles travel along the detection portion of the flow channel. The controller may be coupled to the first and second light sources so as to modulate the first light source at a first modulation frequency v1, and to modulate the second light source at a second modulation frequency v2 different from v1. The signal processing unit may be coupled to the detector to receive the detector output. The signal processing unit may provide a system output based on the detector output. The system output may provide a first measure of the particles of the first particle type in the sample and a second measure of the particles of the second particle type in the sample.

We also disclose methods for analyzing samples that may comprise particles of at least a first and second particle type.

Such methods may include passing the sample through a flow channel, illuminating the sample in a first excitation portion of the flow channel with first excitation light from a first light source while the sample flows through the flow channel, and illuminating the sample in a second excitation portion of the flow channel with second excitation light from a second light source while the sample flows through the flow channel. The first excitation light may stimulate a first light emission from particles of the first particle type, and the second excitation light may stimulate a second light emission from particles of the second particle type. The methods may also include detecting at least a portion of the first and second light emission with a detector adapted to provide a detector output based on the received light emission. The illuminating may be carried out such that the first excitation light is modulated at a first modulation frequency v1, and the second excitation light is modulated at a second modulation frequency v2 different from v1.

In some cases, the first and second excitation portions of the flow channel may overlap with each other and with a detection portion of the flow channel, and the method may also include spatially modulating light emitted from particles in the detection portion of the flow channel, such that the first and second light emission is detected by the detector with a third modulation frequency different from the first and second modulation frequencies, the third modulation frequency being based on a flow rate of the sample through the flow channel. The spatially modulating may include providing a mask between the detection portion of the flow channel and the detector. In some cases, the spatially modulating may include imaging the mask onto the detection portion of the flow channel.

The modulation of the first excitation light may be periodic, and the modulation of the second excitation light may also be periodic, but at a different frequency. Furthermore, the spatial modulation of the light emitted from particles in the detection portion of the flow channel may also be periodic.

The first light emission may have a first intrinsic response time and an associated first intrinsic frequency, and the first modulation frequency may be less than the first intrinsic frequency. Likewise, the second light emission may have a second intrinsic response time and an associated second intrinsic frequency, and the second modulation frequency may be less than the second intrinsic frequency. The method may also include performing a frequency analysis of the detector output, the frequency analysis including identifying one or more peaks in a frequency spectrum of the detector output.

Related methods, systems, articles, and components are also discussed.

These and other aspects of the present application will be apparent from the detailed description below. In no event, however, should the above summaries be construed as limitations on the claimed subject matter, which subject matter is defined solely by the attached claims, as may be amended during prosecution.

BRIEF DESCRIPTION OF THE DRAWINGS

In the figures, like reference numerals designate like elements.

DETAILED DESCRIPTION OF ILLUSTRATIVE EMBODIMENTS

The strategic landscape for biological and biomedical testing and analysis is undergoing a transformation. Today, the majority of tests are performed at major, centralized clinical laboratories. This is in part because compact, robust, and inexpensive instruments for point of care (POC) testing are not available. Principal drivers for POC testing are reducing costs, obtaining timely test results, lowering mortality rates, and reducing morbidity. Commercial flow cytometers are sophisticated analytical instruments extensively used in research and clinical laboratories. They do not, however, meet the challenging practical requirements of POC testing.

In conventional flow cytometry, the size of the excitation area is restricted approximately to the size of the particle to be detected. In contrast, the techniques disclosed herein may use a much larger excitation region to increase the total flux of detected light that emanates from a particle of interest. In combination with the large excitation area, spatial filtering can be employed to enable a high spatial resolution in the micron range. This may allow for independently detecting and characterizing particles with a separation (in the flow direction) that can approach the dimension of individual particles. Also, the disclosed techniques can be intrinsically tolerant to background fluorescence originating from fluorescent components in solution, fluorescent components of the detection apparatus, and surface contaminants.

Figure 1:
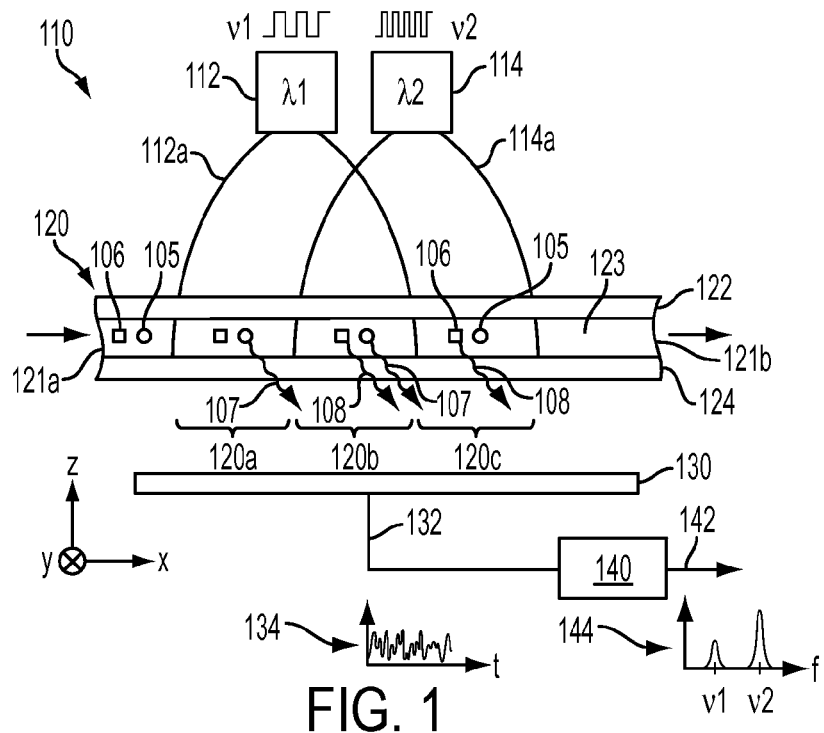
FIG. 1 is a schematic side or sectional view of a sample analyzer.

An illustrative sample analyzer 110 is shown schematically in FIG. 1, in the context of a Cartesian x-y-z coordinate system for reference purposes. The analyzer includes light sources 112, 114, a fluid handling device 120, and a detector 130. The fluidic device 120 is adapted to receive a sample of interest to be analyzed. The sample may enter the device 120 at an inlet 121a thereof and exit the device 120 at an outlet 121b thereof, flowing generally along the x-direction through a flow channel 123 formed between confining members 122, 124. The members 122, 124 may be or comprise plates or sheets of glass, plastic, or other suitable materials. One or both of members 122, 124 may be a microscope slide or a microscope cover glass, or portion thereof. The members 122, 124 need not, however, be planar in shape. For example, they may be portions of a unitary tube or pipe of circular cross section. Other non-planar shapes are also contemplated. In some cases, confinement of the sample may not be necessary, whereupon one or both of members 122, 124 may be omitted.

At least a portion of the confining member 122 is transmissive to excitation light emitted by the light sources 112, 114. In that regard, light source 112 emits first excitation light in a first light beam 112a towards the fluidic device 120, and light source 114 emits second excitation light in a second light beam 114a towards the fluidic device 120. "First" and "second" will be understood to be arbitrary terms used for identification purposes only, and are not intended to be limiting. The first excitation light comprises light of a first wavelength $\lambda 1$, and the second excitation light comprises light of a second wavelength $\lambda 2$. The first excitation light may have a peak output at $\lambda 1$, and the second excitation light may have a peak output at $\lambda 2$. In most cases it is desirable for the excitation light from both sources to be relatively narrow band light, such as the light emitted by typical laser sources. However, extremely narrow bandwidth light (such as that of certain narrow linewidth laser sources) is not necessary in general. In some cases, for example, one or both of the light sources may comprise a conventional light emitting diode (LED) source or a resonant cavity LED (RC-LED) source, which may emit light in a bandwidth (measured in terms of full width at half maximum, or FWHM) of 5 to 60 nm, for example. If desired, the light source may incorporate one or more filters to narrow or otherwise tailor the spectrum of the resultant output light.

Whichever light sources are selected, the spectral makeup or composition of the excitation light emitted by the sources 112, 114 is preferably different enough from each other so that they preferentially excite light emission from different particle types that may be present in the sample. To achieve this, in many cases it is desirable for the first excitation light to contain little or no light of the second wavelength $\lambda 2$, and for the second excitation light to contain little or no light of the first wavelength $\lambda 1$, and for $\lambda 1$ to be sufficiently different from $\lambda 2$.

The confining member 122 transmits both light beams 112a, 114a such that they illuminate the sample disposed within the flow channel 123. For generality, the figure shows the excitation light beams illuminating different but overlapping excitation portions of the flow channel 123. The first excitation light beam 112a illuminates a first excitation portion of the flow channel 123, the first excitation portion shown in FIG. 1 to consist essentially of the adjacent regions 120a and 120b of the flow channel. The second excitation light beam 114a illuminates a second excitation portion of the flow channel 123, the second excitation portion shown in FIG. 1 to consist essentially of the adjacent regions 120b and 120c of the flow channel. The sample is depicted as containing two types of particles: first particles 105, and second particles 106. In the figure, the first excitation light is depicted as exciting the first particles 105 (and not the second particles 106) residing in regions 120a or 120b, such first particles emanating light 107 in response to the excitation. The second excitation light is depicted as exciting the second particles 106 (and not the first particles 105) residing in regions 120b or 120c, such second particles emanating light 108 in response to the excitation. Light emission from the particles is depicted only schematically in the figure, but the reader will understand that a given excited particle typically emits light in all directions.

The term "particle" will be understood by the reader to refer broadly to an object of interest to be detected. In most applications, particles of interest are relatively small, and may be microscopic in size. A given particle of interest may be or include one or a collection of biological cell(s), virus(es), molecule(s), sub-molecular complex(es), bead(s) (including microbeads), droplets (e.g. oil in water), gas bubbles, or other bit(s) of matter, for example. Cells or other particles may be treated, e.g., stained or tagged with a suitable fluorescent probe or other agent, in such a way that they emit light in a predictable fashion when illuminated with excitation light. In this regard, the light emitted by a given excited particle may be fluorescent in nature, or it may constitute a form of scattered light such as in the case of Raman scattering. The reader will therefore understand that when we refer to, for example, incident light that is effective to excite a particle, such incident excitation light may be selectively absorbed by the particle so as to cause the particle to fluoresce, or such incident excitation light may selectively interact in some other way with the particle, e.g. so as to cause resonant Raman scattering. In any case, the emitted light is preferably shifted in wavelength to some extent relative to the excitation light so that at least a portion of the emitted light can be at least partially isolated from the excitation light with one or more suitable filters. Whatever the nature of the light emitted by a particle of interest, such emitted light also preferably responds relatively rapidly to excitation light so that if the excitation light is modulated at a particular frequency $\nu$, the emitted light will also fluctuate to some measurable extent at the frequency $\nu$.

Emanating light 107 emitted by the first particles 105 may or may not have a substantially different spectral composition from emanating light 108 emitted by the second particles 106. In most cases, any differences in spectral composition between light emanating from the various particle types to be detected are ignored by the photosensitive detector 130 used in the analyzer. The photosensitive detector 130 in such cases may merely be designed to provide an output current, voltage, or other output signal that responds both to the amount of light impinging on the detector from the first particle(s), and to the amount of light impinging on the detector from the second particle(s).

The confining member 124, or at least a portion thereof, substantially transmits the emanating light 107, 108 originating from the various excited particles in the flow channel. The transmitted emanating light is thereafter intercepted by the photosensitive detector 130, which converts the intercepted light into a current, voltage, or other measureable parameter. In exemplary embodiments, the detector 130 is a single large area detector that provides only one output, such output varying in time in accordance with the light impinging on the active surface of the detector. In other cases, the detector may include a plurality or array of distinct photosensitive devices. In any case, the detector collects light emanating from particles residing in a specific portion, referred to as a detection portion, of the flow channel. The detection portion of the flow channel may be determined or defined as a function of the size and placement of the detector, design details of the flow channel, the presence of any lenses, mirrors, masks, apertures, or other optical components (not shown in FIG. 1) that may be placed between the detector and the flow channel, and so forth. The detection portion of the flow channel overlaps at least in part with the first excitation portion of the flow channel, and it also overlaps at least in part with the second excitation portion of the flow channel. In some cases, the detection portion, the first excitation portion, and the second excitation portion may all substantially coincide with each other.

Exemplary photosensitive detectors that may be used in the disclosed systems, depending on the design specifications of the analyzer, include robust solid-state devices such as conventional photodiodes and avalanche photodiodes (APDs). Silicon photodiodes are responsive over a wavelength range from roughly 300 nm to 1.1 microns, and are plentiful, rugged, reliable, and relatively inexpensive. Numerous other types of photodiodes are also available, such as germanium, indium gallium arsenide (InGaAs), and extended-InGaAs, to name only a few. If desired, any other type of photosensitive detector may also be used, including, for example, one or more photomultiplier tubes. The detector may be of hybrid design, and in that regard may include one or more preamplifiers, thermoelectric coolers, and/or other features or capabilities.

Whichever type of detector 130 is used, the detector generates an output on line 132, which may be supplied to signal processing unit 140. In a simple design, the line 132 may be or comprise a coaxial cable, or a twisted pair of wires. The line 132 carries a time varying output signal, depicted schematically as output 134. The signal processing unit 140 may perform an analysis on the output signal 134. The analysis may include, for example, measuring correlation(s) with one or more other signals, and/or evaluating the frequency content of the output signal. The results of the analysis may be used to provide one or more measures of the particles 105, 106 in the sample, e.g., absolute or relative amounts of such particles in the sample, particle speeds and speed distributions, particle sizes, and so forth. The signal processing unit 140 may comprise one or more microprocessors and/or microcontrollers, and/or one or more application specific integrated circuits (ASICs), and/or one or more field-programmable gate arrays (FPGAs), and/or any other digital signal processing (DSP) circuitry. The signal processing unit may also optionally include volatile and/or non-volatile memory, storage device(s), and software. Software, hardware, and/or firmware may be tailored to carry out frequency analysis of one or more a time-varying signal, e.g., a set of instructions to carry out a fast Fourier transform (FFT) procedure or other Fourier transform or other transform procedure. In some cases, the signal processing unit may be or comprise a desktop, laptop, notebook, or other portable or non-portable computer system, including e.g. mobile phones, smart phones, or any other type of personal digital assistant, suitably equipped with appropriate interfaces, networks, hardware, and software to carry out the desired signal analysis.

In order to allow the signal processing unit 140 to distinguish between signal components in the output signal 134 due to particles of the first type, and signal components in the output signal 134 due to particles of the second type, the sources 112, 114 are modulated at different respective modulation frequencies $\nu_1, \nu_2$. Drive signals of these frequencies are depicted schematically in FIG. 1. The drive signals are preferably periodic. The drive signals may be substantial square waves, as shown in the figure, or they may have duty cycles greater or less than 50% or they may have any other shape (e.g., sinusoidal or ramped) as desired. Preferably, however, the drive signal for source 112 contains a dominant frequency component at frequency v1, and the drive signal for source 114 contains a dominant frequency component at frequency v2. In this regard, a "dominant frequency" or "dominant frequency component" may refer to a frequency at which the Fourier signal power or other relevant frequency-based function exhibits a dominant peak, the dominant peak being greater in magnitude than all other function values of the frequency-based function, other than 1/f noise for frequencies approaching zero.

The modulation of any one of the light sources may be accomplished directly or indirectly. In a direct modulation approach, a drive signal that powers or energizes the light source may be modulated, and the drive signal modulation may then directly translate into substantially the same modulation of the excitation light provided by the light source. Direct modulation is advantageous insofar as it typically requires no additional optical or mechanical parts, and is flexible and convenient. In an indirect approach, the light source may include a lamp or source in combination with a shutter device. The lamp or source in such cases may emit excitation light at a constant output level, and modulation may be provided by the shutter device. The shutter device may be mechanical, e.g. as in the case of a chopper wheel or a segmented scanning mirror, or it may be electro-optical with no moving parts, e.g. as in the case of a Kerr cell, Pockels cell, acousto-optic tunable filter (AOTF), or electro-optical modulator, for example.

The frequencies v1, v2 are preferably selected to be slower than the frequencies associated with the characteristic response time of the respective sources 112, 114, so that the fluxes or intensities of the first and second excitation light beams 112a, 114a are modulated in substantially the same manner as the drive signals for the respective light sources. For example, if a given source has a characteristic response time of 10 ns, the drive frequency v for that source is desirably less than 100 MHz (=1/10 ns). Moreover, the frequencies v1, v2 are also preferably selected to be slower than the characteristic response time of the emanating light 107, 108 of the respective particles 105, 106 (e.g. in the case of fluorescence, the 1/e fluorescent decay time τ), so that the fluxes or intensities of the first and second excitation light beams 112a, 114a are modulated in substantially the same manner, or at least in a similar manner, as the drive signals for the respective light sources and the excitation beams emitted by those sources. For example, if the light emission of a given particle type has a characteristic decay time of 1 µs, the drive frequency v for the source responsible for the excitation of that particle is desirably less than 1 MHz (=1/(1 µs)).

Note that the lowest level or "baseline" for the drive signals, and for the associated modulated excitation beams and the emanating light from the particles, can be zero, but in general it need not be zero. Any given drive signal may oscillate between an upper level and a lower level, and the lower level may be zero or it may be an intermediate level between zero and the upper level. In the case of laser diode light sources, the use of an intermediate level above the laser threshold can achieve faster modulation speed and reduced wavelength chirp. Likewise, the flux or intensity of any given excitation beam may oscillate between an upper level and a lower level, and the lower level may be a completely dark or "off" state, or it may be an intermediate "on" state between the dark state and the upper level. Similarly, the flux or intensity of light emitted by any given particle located in the excitation portion of the flow channel may oscillate between an upper level and a lower level, and the lower level may be a completely dark or "off" state, or it may be an intermediate "on" state between the dark state and the upper level.

In view of the fact that the detector 130 may respond to light emanating from the different particle types without any ability to inherently distinguish between such emanating light, differential modulation of the emanating light, which is brought about by differential modulation of the excitation light, which in turn is brought about by differential modulation of the drive signals for the light sources, is employed. The differential modulation allows the signal processing unit 140 to distinguish between signal components in the output signal 134 associated with particles of different types by merely evaluating the frequency content of the output signal 134. The unit 140 may, for example, calculate a Fourier transform (e.g. using a Fast Fourier Transform (FFT) technique or other suitable technique) or other suitable frequency spectrum of the output signal 134 or a portion thereof. Such a frequency spectrum is shown schematically as spectrum 144 in FIG. 1. If the frequency spectrum includes a significant contribution (e.g. in the form of a local peak in the frequency spectrum) at a frequency v equal to the modulation frequency v of one of the light sources, that contribution corresponds to a signal component of the same frequency v in the output signal 134, which in turn is indicative of the presence of a particle of a particular type in the detection portion of the flow channel 123. In the case of analyzer 110, a frequency component at a frequency f=v1 is indicative of the presence of a first particle 105 in the first excitation portion and the detection portion of the flow channel 123. Similarly, a frequency component at a frequency f=v2 is indicative of the presence of a second particle 106 in the second excitation portion and the detection portion of the flow channel 123.

Information relating to particle size, and/or the number or particles of a given type that are present in the flow channel at a given time, may be obtained by measuring the amplitude or strength of the signal component at the relevant frequency, e.g., the amplitude of the frequency spectrum 144 at the relevant frequency. Note that particles of different types may be present at the same time in the (excitation and detection portions of the) flow channel, and the signal processing unit 140 will still be capable of distinguishing such particles based on the frequency evaluation or analysis of the output signal 134. Note also that the detection of a signal component at a given modulation frequency v1 or v2 does not by itself provide any information about the speed of the detected particle in the flow channel 123, because detected signal components at those frequencies are independent of particle speed. However, at least in cases where the particle density is low enough so that only a single particle (at most) is likely to be present in the detection portion of the flow channel at any given time, then particle speed information may in some cases be obtained by measuring the time duration of the signal component associated with the particle, combined with information relating to the longitudinal dimension (i.e., the dimension along the direction of flow, or along the x-direction in FIG. 1) of the detection portion and/or the relevant excitation portion of the flow channel. The longitudinal dimension of the relevant portion of the flow channel divided by the time duration of the signal component may produce a measure of the particle speed.

In order to provide optimal signal detection with minimal chance for signal misidentification, it is advantageous for the modulation frequencies v1, v2 to satisfy certain relationships beyond those discussed above. In particular, it is advantageous for the various modulation frequencies to not be related as harmonics. Thus, v1 is preferably not an integer multiple of v2, and v2 is preferably not an integer multiple of v1.

The analyzer 110 is a system containing n light sources modulated at n distinct frequencies to detect at least n different particle types in a sample. For simplicity, n has been assumed to be 2. The reader will, however, readily appreciate that the analyzer 110 can be extended in a straightforward way to cases in which n=3, 4, or more. For example, if n=3, a third light source can be added, the third light source emitting third excitation light at a third wavelength λ3, the third excitation light preferentially exciting particles of a third particle type rather than particles of the first and second particle types. The third light source can then be modulated at a modulation frequency ν3 different from ν1 and ν2. The signal processing unit 140 may be configured to evaluate the frequency content of the time-varying output signal 134 not only at the frequencies ν1 and ν2, but also at ν3. Furthermore, the number of particle types that can be differentiated can be greater than the number of modulated light sources included in the analyzer system. For example, even if the system includes only two light sources, modulated at respective frequencies ν1, ν2, the system may employ analysis techniques discussed elsewhere herein to allow more than two particle types to be differentiated.

Other analyzers discussed herein are also described as 2-channel systems for simplicity, i.e., systems that detect at least two different particle types at two distinct modulation frequencies, but the reader will understand that such other analyzers can also be readily extended to n channels, where n may by 3, 4, or more as desired.

Figure 2:
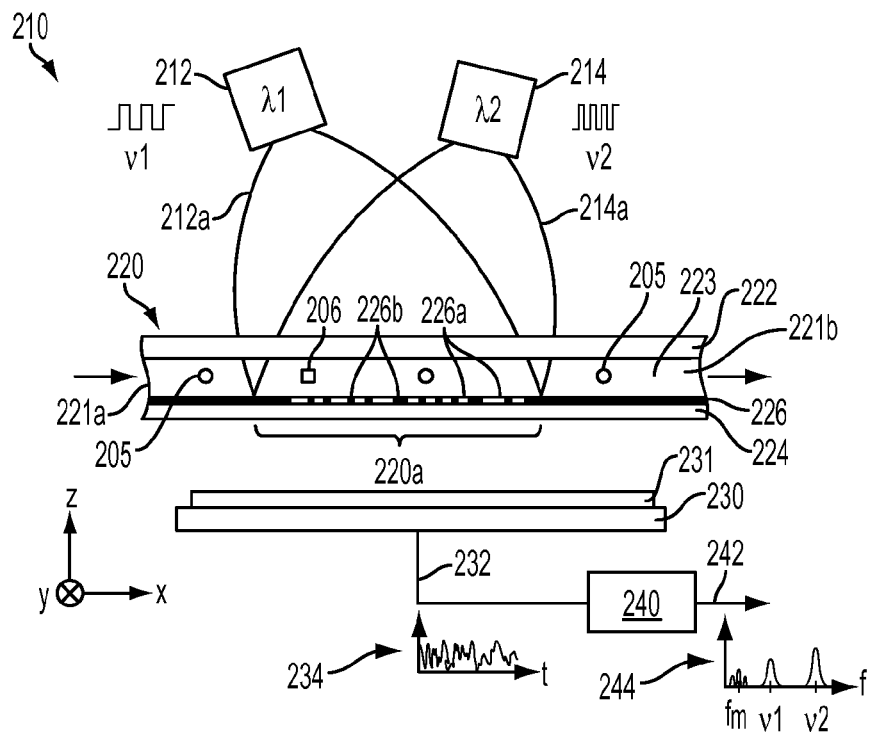
FIG. 2 is a schematic side or sectional view of another sample analyzer.

Another such sample analyzer 210 is shown schematically in FIG. 2. The analyzer 210 is similar in many respects to the analyzer 110 of FIG. 1, but with differences that will be discussed presently. For brevity, features of the analyzer of FIG. 1 and its components discussed above will be understood to apply equally to corresponding aspects and components of the analyzer of FIG. 2. For example, without limitation, features of the light sources and the modulation thereof, features of the flow channel, features of the photosensitive detector, and features of the signal processing unit will all be understood as applying equally to the analyzer of FIG. 2, unless otherwise indicated. More generally, features discussed in connection with any of the embodiments herein should be understood as also applying (as optional features or modifications) to all other disclosed embodiments, unless otherwise indicated.

Similar to analyzer 110 of FIG. 1, the analyzer 210 includes light sources 212, 214, a fluid handling device 220, and a detector 230. The fluidic device 220 is adapted to receive a sample of interest to be analyzed. The sample may enter the device 220 at an inlet 221a thereof and exit the device 220 at an outlet 221b thereof, flowing generally along the x-direction through a flow channel 223 formed between confining members 222, 224.

At least a portion of the confining member 222 is transmissive to light emitted by the light sources 212, 214. In that regard, light source 212 emits first excitation light in a first light beam 212a, comprising a first wavelength λ1, towards the fluidic device 220, and light source 214 emits second excitation light in a second light beam 214a, comprising a second wavelength λ2, towards the fluidic device 220. The spectral makeup or composition of the excitation light emitted by the sources 212, 214 is preferably different enough from each other so that they preferentially excite light emission from different particle types that are suspected to be present in the sample.

The confining member 222 transmits both light beams 212a, 214a such that they illuminate the sample disposed within the flow channel 223. In contrast to FIG. 1, FIG. 2 shows the excitation light beams illuminating substantially the same excitation portion 220a of the flow channel 223, i.e., complete overlap of the first and second excitation portions. System 110 of FIG. 1 also of course may be modified to incorporate this feature, and system 220 can be implemented with only partially overlapping excitation regions. The sample is depicted as containing two types of particles: first particles 205, and second particles 206. The first excitation light preferentially excites the first particles 205 (and not the second particles 206) residing in region 220a, such first particles emanating light (not shown in FIG. 2) in response to the excitation. The second excitation light preferentially excites the second particles 206 (and not the first particles 205) residing in region 220a, such second particles emanating light (not shown in FIG. 2) in response to the excitation.

Just as mentioned above in connection with FIG. 1, emanating light emitted by the first particles 205 may or may not have a substantially different spectral composition from emanating light emitted by the second particles 206. In many cases, any differences in spectral composition between light emanating from the various particle types to be detected are ignored by the photosensitive detector 230 used in the analyzer. The photosensitive detector 230 in such cases may merely be designed to provide an output current, voltage, or other output signal that responds both to the amount of light impinging on the detector from the first particle(s), and to the amount of light impinging on the detector from the second particle(s). This technique can of course also be combined with multi-color detection (typically realized with multiple detectors with different dichroic mirror and/or filter combinations) as used in conventional flow cytometry. This increases the complexity of the system but allows it to distinguish between even more different particle types.

The confining member 224, or at least a portion thereof, substantially transmits the emanating light originating from the various excited particles in the flow channel. The transmitted emanating light is thereafter intercepted by the photosensitive detector 230, which converts the intercepted light into a current, voltage, or other measurable parameter. The detector collects light emanating from particles residing in a specific portion, referred to as a detection portion, of the flow channel. The detection portion of the flow channel overlaps at least in part with the first and second excitation portions of the flow channel, i.e., with portion 220a, and it may substantially coincide with such portion 220a.

In order to help separate the typically weak or dim emanating light from the excited particles from the typically much stronger or brighter excitation light from the light sources, an optical filter 231 may be provided between the detector and the flow channel. The optical filter 231 preferentially blocks, e.g. by reflection, absorption, scattering, or any other know mechanism, the first and/or second excitation light 212a, 214a, and preferentially transmits light emanating from the excited particles in the detection portion of the flow channel. An optical filter such as optical filter 231 is sometimes needed or desired to prevent the detector 230 and/or its amplifier circuit(s) from experiencing saturation, and to allow lower noise detection of the emanating light from the particles. Such an optical filter may of course also be incorporated into the analyzer 110 of FIG. 1. Other techniques can also be used to minimize the amount of excitation light reaching the detector. For example, the excitation light may be directed along a path or axis that does not intersect the detector. In the case of FIG. 2, the filtered detector may be shifted to a position that is (from the perspective of FIG. 2) above or below the plane of the figure, such that a line drawn from the center of the detection portion of the flow channel to the center of the detector is parallel to the y-axis, and perpendicular to a line drawn from the center of either or both light sources to the center of the detection portion of the flow channel. Alternatively, the sources 212, 214 may be shifted to similar positions, such that the beams 212a, 214a are directed along axes that lie in the x-y plane rather than in the x-z plane, for example.

Similar to FIG. 1, the detector 230 generates an output on line 232, which may be supplied to signal processing unit 240. The line 232 carries a time varying output signal, depicted schematically as output 234. The signal processing unit 240 may perform an analysis on the output signal 234, which analysis may be the same as or similar to the analysis discussed in connection with FIG. 1. In order to allow the signal processing unit 240 to distinguish between signal components in the output signal 234 due to particles of the first type, and signal components in the output signal 234 due to particles of the second type, the sources 212, 214 are modulated at different respective modulation frequencies $v1$, $v2$. The differential modulation allows the signal processing unit 240 to distinguish between signal components in the output signal 234 associated with particles of different types by merely evaluating the frequency content of the output signal 234. The unit 240 may, for example, calculate a Fourier transform or other suitable frequency spectrum of the output signal 234 or a portion thereof. Such a frequency spectrum is shown schematically as spectrum 244 in FIG. 2. A frequency component at a frequency $f=v1$ is indicative of the presence of a first particle 205 in the first excitation portion and the detection portion of the flow channel 223, and a frequency component at a frequency $f=v2$ is indicative of the presence of a second particle 206 in the second excitation portion and the detection portion of the flow channel 223.

Information relating to particle size, and/or the number or particles of a given type that are present in the flow channel at a given time, may be obtained by measuring the amplitude or strength of the signal component at the relevant frequency, e.g., the amplitude of the frequency spectrum 244 at the relevant frequency. Note that particles of different types may be present at the same time in the (excitation and detection portions of the) flow channel, and the signal processing unit 240 will still be capable of distinguishing such particles based on the frequency evaluation or analysis of the output signal 234. Note also that the detection of a signal component at a given modulation frequency $v1$ or $v2$ does not by itself provide any information about the speed of the detected particle in the flow channel 223, because detected signal components at those frequencies are independent of particle speed. However, at least in cases where the particle density is low enough so that only a single particle (at most) is likely to be present in the detection portion of the flow channel at any given time, then particle speed information may in some cases be obtained by measuring the time duration of the signal component associated with the particle, combined with information relating to the longitudinal dimension (i.e., the dimension along the direction of flow, or along the x-direction in FIG. 2) of the detection portion and/or the relevant excitation portion of the flow channel.

The analyzer 210 of FIG. 2 includes a significant additional component that was not included in the analyzer of FIG. 1, the additional component allowing for additional or more precise information to be obtained regarding the particles of interest in the sample to be tested. The additional component is a spatial filter 226. In some cases, the spatial filter 226 may be in the form of a patterned mask. The spatial filter is disposed between the flow channel 223 and the detector 230, and it is adapted to transmit light emanating from the excited particles in the flow channel by varying amounts as the particles travel along the detection portion of the flow channel. This variable transmission is preferably achieved with a longitudinal sequence or pattern of transmissive regions 226a and non-transmissive regions 226b. As an excited particle travels along the detection portion of the flow channel, light emanating from such particle is alternately transmitted to the detector 230 and blocked from reaching the detector 230, the alternate transmission and non-transmission producing another distinguishable time-varying component in the time-varying output signal 234. Unlike the time-varying components associated with the modulation of the light sources 212, 214, the additional time-varying component associated with the spatial filter 226 is dependent on the speed, and position, of the excited particle. Due to the presence of this additional modulation in the output signal 234, additional frequency components disposed generally at a mask frequency $f_m$ are depicted in the frequency spectrum 244 of FIG. 2.

The spatial filter 226 is disposed between the flow channel 223 and the detector 230, and in FIG. 2 it is shown to be disposed at the flow channel. If desired, the spatial filter 226 may be disposed at other positions at the flow channel, e.g., embedded within the confining member 224, or disposed on the lower major surface (from the vantage point of FIG. 2) of the confining member 224. The spatial filter 226 may also be oriented differently along with the detector; for example, the spatial filter 226 may be reoriented to reside in the x-z plane rather than in the x-y plane. Also, rather than being disposed at the flow channel, the spatial filter 226 may be remote from the flow channel, and one or more lens(es) and/or mirror(s) may be used to image the spatial filter onto the flow channel so that it can still provide, from the standpoint of the detector, modulation of light emanating from moving particles. The imaging system provided by the lens(es) and/or mirrors) may introduce magnification, such that the actual or physical spatial filter 226 is larger or smaller than its image at the flow channel in accordance with the magnification factor of the imaging system. In view of the distinction in remote filter arrangements between the physical spatial filter and the imaged spatial filter, in discussions herein involving spatial filters, the reader should interpret references to the spatial filter as referring to the imaged spatial filter rather than the physical spatial filter, unless otherwise indicated to the contrary.

The pattern or sequence of transmissive regions 226a and non-transmissive regions 226b in the spatial filter 226 define a transmission function that changes based on longitudinal position, i.e., based on position measured along the x-direction or flow direction. This transmission function may be substantially periodic, or it may instead be substantially non-periodic. An example of a periodic transmission function is a square wave, or a rectangle wave of constant period. A limitation of periodic transmission functions is that they do not typically allow for high spatial resolution of a detected particle. However, this limitation may be unimportant in cases of rare event detection, i.e., in cases where the particle density is low enough so that only a single particle (at most) is likely to be present in the detection portion of the flow channel at any given time. Examples of this may include pathogen detection in water, or rare cell scanning. Another advantage of a periodic transmission function is its ability to produce a clear, strong peak in the frequency spectrum (see e.g. spectrum 244) of the detector output signal, for a single particle moving at a constant speed in the detection region.

An example of a non-periodic transmission function is a random function, or a chirped function (having a monotonically increasing or decreasing period). An advantage of non-periodic transmission functions is that they do typically allow for high spatial resolution of a detected particle, by employing correlation techniques to determine the longitudinal position of the particle at a given moment in time. For example, a correlation may be carried out between the time-varying detector output 234 and a signal template representative of the (non-periodic) transmission function. The presence and location of a peak in the correlation can be used to determine the precise position of the particle along the length of the spatial filter 226. This capability is not limited to rare event detection, and can be used with higher particle densities in which multiple particles are present in the detection portion of the flow channel at a given time.

One characteristic of the spatial filter worth noting is its "minimum feature size" ("MFS"). The MFS refers to the length, as measured along the longitudinal direction (i.e., the flow direction, e.g., the x-direction in FIGS. 2 and 3), of the shortest identifiable region of the spatial filter. The shortest identifiable region may in some cases be a transmissive region, while in other cases it may be a non-transmissive region, while in still other cases it may be both a transmissive region and a non-transmissive region (i.e., if the shortest transmissive region has the same longitudinal length as the shortest non-transmissive region, or if all transmissive regions have the same longitudinal length as all non-transmissive regions). The MFS of the spatial filter used in an analyzer has a direct impact on the spatial resolution of the analyzer, with larger MFSs generally corresponding to lower spatial resolutions. Of course, the average or typical particle size also has an impact on spatial resolution. In many cases, it is desirable to design the spatial filter such that the MFS is on the order of the largest average particle size or somewhat greater, e.g., one to two times the average particle size for the largest particle type of interest to be detected.

The spatial filter 226 may be substantially monochromatic, or it may be polychromatic as in the case of a color filter assembly. In a monochromatic spatial filter, the transmissive regions 226a all have substantially the same transmission characteristic, and the non-transmissive regions 226b also all have substantially the same transmission characteristic (but different from that of the transmissive regions). In a simple case, the transmissive regions 226a may all be completely clear, as in the case of an aperture, and the non-transmissive regions 226b may be completely opaque, as in the case of a layer of black ink or other absorptive, reflective, or scattering material. Alternatively, the transmissive regions 226a may all have a given color or filter characteristic, e.g., high transmission for light emanating from excited particles, but low transmission for excitation light. Alternatively, the non-transmissive regions may have a low but non-zero light transmission, as in the case of a grey ink or coating, or a partial absorber or reflector.

In a polychromatic spatial filter, at least two different types of transmissive regions 226a are provided: first transmissive regions having a first transmission characteristic, and second transmissive regions having a second transmission characteristic, each of these transmission characteristics being different from the (usually opaque or nearly opaque) transmission characteristic of the non-transmissive regions. The first transmission characteristic may correspond to a first filter type, and the second transmission characteristic may correspond to a second filter type. In cases where the first particle type has an emission spectrum that is substantially different from that of the second particle type, the transmission characteristics of the first and second transmissive regions can be tailored to preferentially transmit emanating light from the first or second particle types, respectively. For example, if the first particle emits light predominantly in the red region of the visible spectrum, and the second particle emits light predominantly in the green region of the visible spectrum, the first transmissive regions may have a higher transmission for red light than for green light, e.g., they may transmit red light and substantially block green light, and the second transmissive regions may have a higher transmission for green light than for red light, e.g., they may transmit green light and substantially block red light. In such cases, the first transmissive regions can be arranged in a periodic fashion with a first spacing or periodicity, and the second transmissive regions can be arranged in a periodic fashion with a different second spacing or periodicity. The different spacings or periodicities provided by the sets of different transmissive regions, together with the fact that the transmission characteristics of these regions are tailored to selectively transmit emanating light from a particular type of particle, can be used to provide two distinct mask frequencies $f_{m1}$, $f_{m2}$ (refer e.g. to mask frequency $f_m$ in FIG. 2) in the frequency spectrum 244 for the different first and second particles, assuming such particles are traveling at a particular (same) speed.

Information regarding spatial filters, sometimes referred to as mask arrangements, filter assemblies, color masks, or the like, can be found in U.S. Pat. No. 7,701,580 (Bassler et al.), in Patent Application Publication U.S. 2010/0201988 (Kiesel et al.), and in pending U.S. patent application Ser. No. 13/113,021, "Analyzers With Time Variation Based on Color-Coded Spatial Modulation", filed May 20, 2011, the entire disclosures of which are incorporated herein by reference, except to the extent they may directly contradict any of the teachings herein.

Regardless of which type of spatial filter 226 is used, a given particle of interest that is present in the detection portion of the flow channel may produce at least two distinct signal components in the detector output 234, which signal components may appear as two distinct frequency components in the frequency spectrum 244. One such component occurs at the modulation frequency of the excitation light source associated with the particle. This component is independent of the flow speed of the particle, and can be used to identify the particle type by matching the peak frequency with the modulation frequency of one of the sources. The other signal component or frequency component preferably occurs at a substantially different frequency, referred to as the mask frequency $f_m$. This component can occur over a range of frequencies $f_m$ depending on the flow speed of the particle and the spatial frequency or periodicity of the spatial filter.

In most cases, the flow speed of the sample (and the particles it contains), the spatial frequency of the spatial filter 226, and the modulation frequencies of the first and second light sources, v1 and v2, are selected such that v1 and v2 are both substantially greater than the range of possible frequencies for $f_m$. Such an arrangement allows the signal processing unit 240 to identify particle type and to independently determine particle speed and/or position without interfering with each other. However, in some cases it may be acceptable or desirable for one or both of v1 and v2 to lie within the range of possible frequencies for $f_m$, or to be substantially less than such range of possible frequencies.

Figure 3:
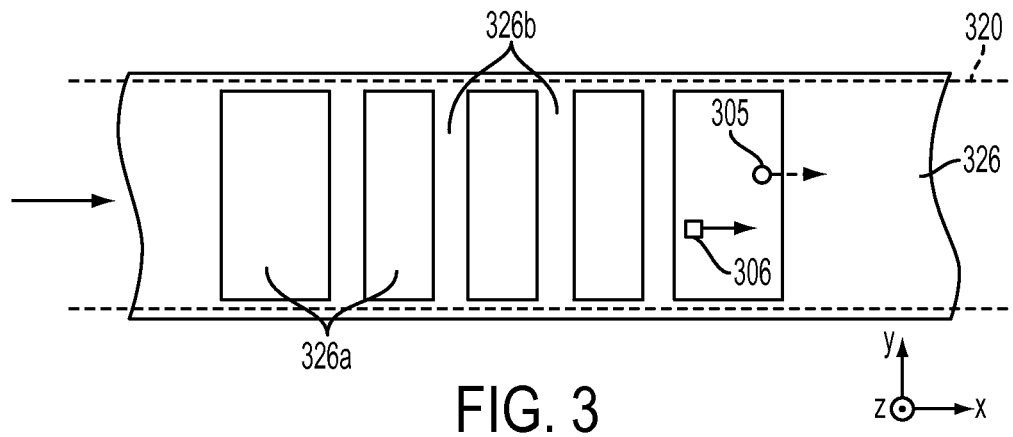
FIG. 3 is a schematic plan or front view of a spatial filter for use in the disclosed analyzers.

Turning now to FIG. 3, we see there a schematic plan or front view of a representative spatial filter 326 that may be used in the disclosed analyzers. The spatial filter 326, which may in some cases be a magnified or de-magnified image of a remotely positioned spatial filter, selectively masks light emanating from particles within the flow channel of a fluid handling device 320. First and second particles 305, 306 are shown to be disposed behind the spatial filter 326, traveling in a flow direction generally parallel to the x-axis. The spatial filter 326 comprises transmissive regions 326a and non-transmissive regions 326b arranged in a pattern along the longitudinal direction. In a simple case, the filter may be an extended film or layer of opaque material in which a number of apertures have been formed. The apertures may correspond to the transmissive regions 326a, and the non-transmissive regions 326b may correspond to the undisturbed opaque material. The longitudinal dimensions (lengths) of the alternating transmissive regions 326a and non-transmissive regions 326b determine the transmission function as a function of position along the x-axis. As discussed above, this transmission function may be substantially periodic or non-periodic. The spatial filter 326 may also be substantially monochromatic, or instead polychromatic.

Figure 4:
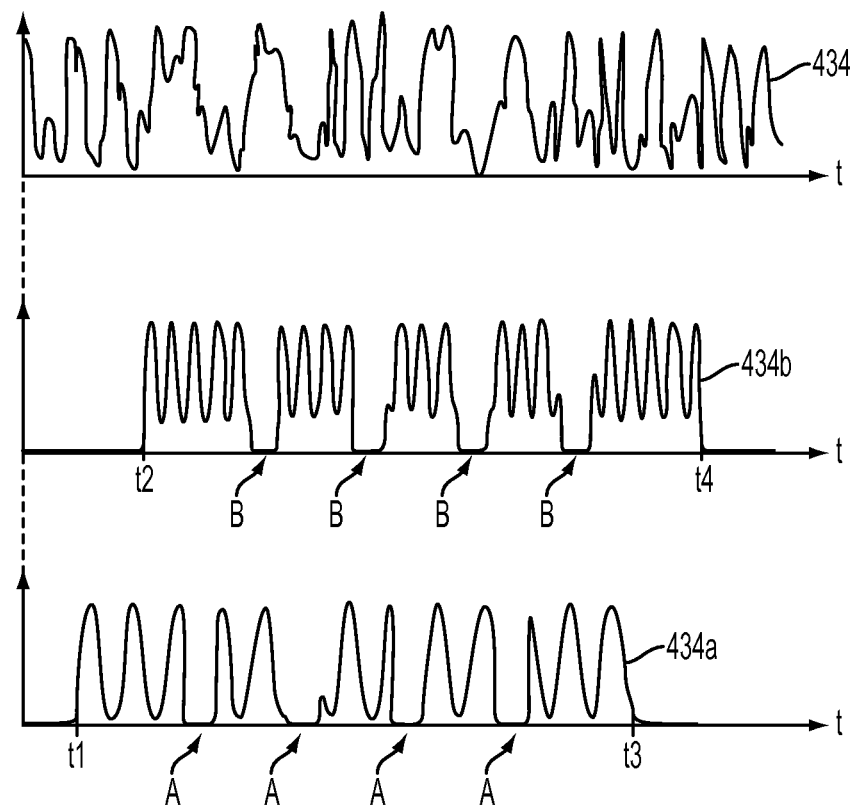
FIG. 4 is a group of graphs that depict idealized signals to assist the reader's understanding of the disclosed techniques, the group including an idealized graph of a representative detector output signal, and idealized graphs of constituent signal components associated with two particles of different particle types.

FIG. 4 is a group of graphs that depict idealized signals to assist the reader's understanding of the disclosed techniques. In the uppermost graph, a representative time-varying detector output signal 434 is shown. The signal 434 may appear on the output of a detector positioned to receive light transmitted by the spatial filter 326 of FIG. 3, as used in a system having modulated light sources such as that of FIG. 2. The lower and middle graphs of FIG. 4 show possible constituent signal components 434a, 434b, respectively, that are combined with other signal components to form the signal 434. The signal 434a represents the signal component provided by a particular first particle 305 (see FIG. 3). The signal 434a begins at a time t1 and ends at a time t3. At the time t1, the first particle 305 passes from a non-transmissive border region to an initial transmissive region 326a at an upstream end of the spatial filter 326. At the times labeled "A", the particle 305 passes behind the four non-transmissive regions that separate the five transmissive regions. At time t3, the particle 305 passes from the final transmissive region 326a at a downstream end of the spatial filter 326 to a non-transmissive border region. The first particle 305 thus enters the detection region of the flow channel at time t1 and exits the detection region at time t3. The high frequency modulation that can be seen in the signal 434a in the time windows corresponding to the transmissive regions 326a represents the variability in the emanating light from the first particle as a result of the modulation of the corresponding light source, e.g., the first light source 212 of FIG. 2.

The signal 434b represents the signal component provided by a particular second particle 306 (see FIG. 3). The signal 434b begins at a time t2 and ends at a time t4. At the time t2, the second particle 306 passes from a non-transmissive border region to the initial transmissive region 326a at an upstream end of the spatial filter 326. At the times labeled "B", the particle 306 passes behind the four non-transmissive regions that separate the five transmissive regions. At time t4, the particle 306 passes from the final transmissive region 326a at the downstream end of the spatial filter 326 to the non-transmissive border region. The second particle 306 thus enters the detection region of the flow channel at time t2 and exits the detection region at time t4. The high frequency modulation that can be seen in the signal 434b in the time windows corresponding to the transmissive regions 326a represents the variability in the emanating light from the second particle as a result of the modulation of the corresponding light source, e.g., the second light source 214 of FIG. 2. Note that the high frequency modulation in the signal 434a is somewhat slower than the high frequency modulation in the signal 434b, because v1 is assumed to be less than v2. Note also that the high frequency modulations in both signals 434a and 434b are faster than the modulation associated with the spatial filter 326. This is because v1 and v2 are assumed in this case to be greater than the modulation associated with the spatial filter (and the speed of the particles).

Figure 5:
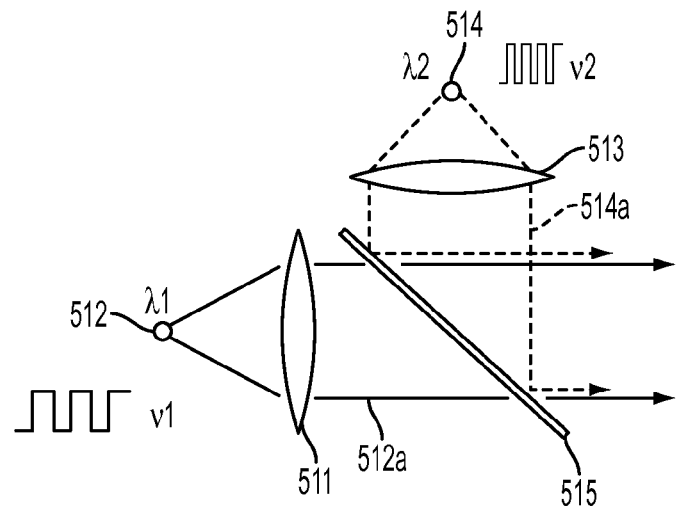
FIG. 5 is a schematic diagram of an arrangement for combining excitation light beams from two light sources.

FIG. 5 is a schematic diagram of one arrangement, out of many possible arrangements, for combining excitation light beams from two independently modulated light sources so that each of the light beams can illuminate a designated excitation region of a flow channel. In this case, light sources 512, 514 have small emitting surfaces and emit excitation light over a range of angles. This excitation light is at least partially collimated by suitable optical elements such as lenses 511, 513, respectively, to produce collimated light beams 512a, 514a as shown. The sources are preferably LEDs or laser diodes capable of direct modulation via a modulated drive current, but any suitable sources of excitation light and modulation techniques may be used. The source 512 emits light in a relatively narrow spectral band centered at wavelength $\lambda 1$ and is modulated at a frequency v1. The source 514 emits light in a relatively narrow spectral band centered at wavelength and is modulated at a frequency v2. A beamsplitter 515 transmits at least some of the light beam 512a and reflects at least some of the light beam 514a such that the resultant beams can be made to substantially overlap with each other, so that they can provide substantially overlapping excitation regions in a flow channel of an analyzer. The flow channel is not shown in FIG. 5 but may be provided at the right side thereof. To minimize losses and maximize signal levels, the beamsplitter may be or comprise a dichroic reflector whose transmissivity is high and reflectivity is low at $\lambda 1$, and whose reflectivity is high and transmissivity is low at $\lambda 2$.

A wide variety of different particle types may be detected using the analyzers disclosed herein, properly configured. Preferably, the particle types have excitation characteristics that are different enough from each other so that light of a given wavelength $\lambda 1$ can excite significant light emission from a first particle type and little or no light emission from a second particle type, and light of another wavelength can excite significant light emission from the second particle type and little or no light emission from the first particle type. In some cases, however, a given light source may excite light emission from both particle types, or both light sources may excite light emission from both particle types, but in different relative amounts.

Figure 6:
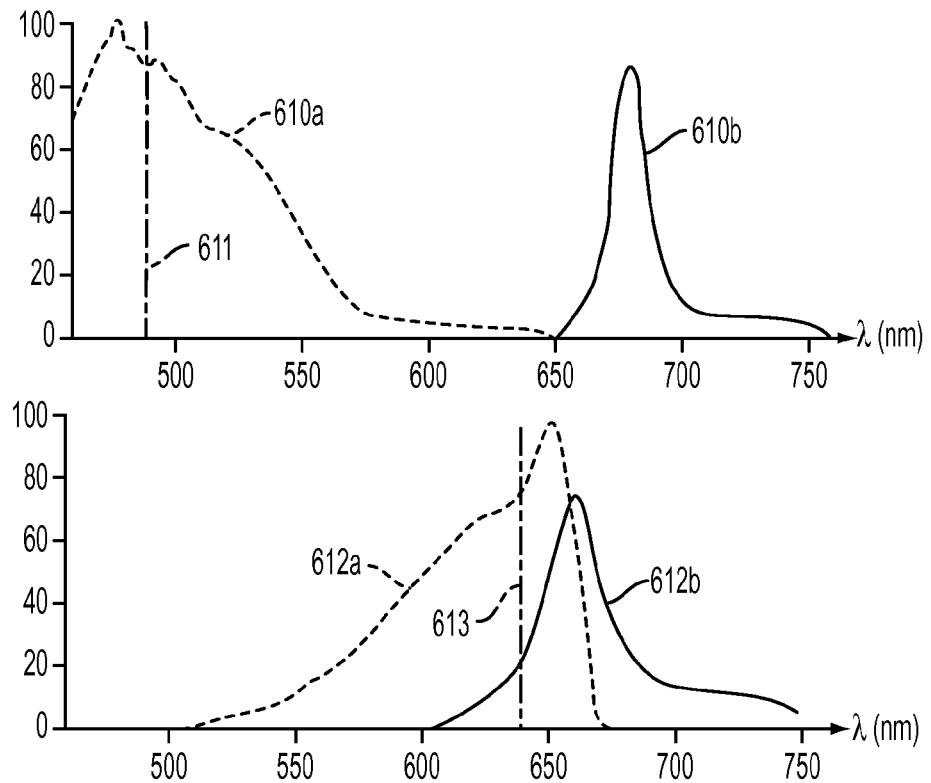
FIG. 6 is a set of two graphs showing an absorption and emission spectrum for two fluorescent probes that may be used to tag different particle types.

FIG. 6 is a set of graphs showing an absorption and emission spectrum for two illustrative fluorescent probes that may be used to tag cells or other particles so as to provide different particle types. In the upper graph, curve 610a represents the absorption spectrum for Peridinin Chlorophyll Protein ("PerCP") complex. Curve 610b represents the emission spectrum for PerCP. In the lower graph, curve 612a represents the absorption spectrum for Allophycocyanin (APC) dye. Curve 612b represents the emission spectrum for APC. One can readily see based on the significant differences between curves 610a and 612a that the excitation characteristics of PerCP and APC are different enough from each other so that light of different wavelengths can be used to selectively excite particles tagged with PerCP and particles tagged with APC. This combination of dyes, having very different (almost complementary) absorption spectra but very similar emission spectra, allows for a very simple implementation in which only a simple long pass emission filter may be used for detection. If more sophisticated emission filters are used, such as those of FIGS. 10 and 11 discussed below, dye combinations that have very different emission spectra, such as cyanine dyes known in the art as Cy3 and Cy 5, can be used. Depending on the application, the available excitation sources, and the emission filter(s) used, a larger variety of dye combinations can be selected using, for example, available internet tools such as the interactive spectrum viewer provided by BD Biosciences, or the interactive spectrum viewer provided by Life Technologies Corporation under the trade designation "invitrogen". The primary desired criterion is that the particle characteristics (e.g., absorption spectra) are different enough so that a first excitation source provides a larger detector signal for a first particle type, and a second excitation source provides a larger detector signal for a second particle type.

In an illustrative example, PerCP and APC may be used for CD4 (or CD8) and CD3 enumeration in a sample of whole blood. A suitable amount of whole blood, such as few microliters, may be mixed with a reagent containing the antibody dye combinations CD4/PerCP and CD3/APC. After a suitable incubation time, e.g., 30 minutes, all cells expressing CD4 on the surface may be tagged with PerCP, thus providing a first particle type, and all cells expressing CD3 on the surface may be tagged with APC, thus providing a second particle type. Such a blood sample may be introduced into any of the analyzers discussed herein, and caused to flow through the flow channel of the analyzer. The characteristics shown in FIG. 6 show that numerous different light sources can be used to independently excite the first and second particle types. We may select, for example, a first laser source operating at $\lambda 1$=488 nm (see line 611 in FIG. 6) and a second laser source operating at $\lambda 2$=638 nm (see line 613 in FIG. 6). Curves 610b, 612b in FIG. 6 reveal that the fluorescent light emitted by the first and second particles (CD4 cells tagged with PerCP, and CD3 cells tagged with APC, respectively) can be readily detected by a single detector, e.g., a silicon photodiode or avalanche photodiode, preferably equipped with a suitable optical filter. The filter may for example be a long pass filter transmitting in a wavelength range above 650 nm, above 660 nm, or it may be a band pass filter transmitting in a wavelength range from about 665 nm to 705 nm, for example. In this illustrative example, the two laser sources can illuminate or target the same excitation region or volume of the flow channel, but they are modulated at different modulation frequencies $v1$, $v2$.

The fluorescent light from both the CD4 and CD3 cells can be measured through the same emission filter with the same detector. The differentiation of the two cell types is encoded in the time-varying output signal of the detector by the modulation frequencies $v1$ and $v2$. Fourier and/or correlation data analysis can be used to extract and distinguish information from the different cell types from the single time-modulated detector signal. Not only can the cell types be distinguished, but an intensity and velocity profile can be extracted for each cell type.

Detection of a peak in the frequency spectrum of the output signal, and matching the detected frequency with $v1$ or $v2$, provides identification of the cell type. In this case, if the detector output signal contains a strong frequency component at frequency $v1$, the cell is a CD4 cell, and if the signal contains a strong frequency component at frequency $v2$, the cell is a CD3 cell.

Correlation is preferably carried out in certain analyzer embodiments that incorporate a spatial filter such as spatial filter 226 of FIG. 2. Correlation of the time-varying output signal of the detector with a template signal representative of the transmission function of the spatial filter may yield the position of the particle, as well as the particle intensity (i.e., the intensity of the emanating light from the particle collected by the detector), which may be indicative of particle size. Particle intensity may alternatively or in addition be determined by measuring the magnitude or amplitude of the frequency spectrum at the modulation frequency $v$ of the light source responsible for exciting the particle.

Figure 7:
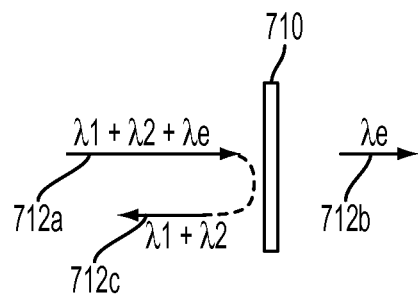
FIG. 7 is a schematic drawing of an optical filter for use in the disclosed analyzers.

FIG. 7 is a schematic drawing depicting the operation of an optical filter 710 used to isolate particle emission from excitation light. The filter 710 is typically placed between the flow channel of the analyzer (not shown in FIG. 7 but assumed to be to the left of the figure) and the photosensitive detector (also not shown in FIG. 7 but assumed to be to the right of the figure). Incident on the filter 710 is light 712a, which may include: light of wavelength $\lambda 1$ from the first excitation source that has passed through the flow channel; light of wavelength $\lambda 2$ from the second excitation source that has passed through the flow channel; and emanating light from the first and second particles in the flow channel, the emanating light assumed for simplicity to comprise a single wavelength $\lambda e$, although the first and second particles may of course in general emit light of different spectra whose peaks occur at different emission wavelengths $\lambda e1$, $\lambda e2$ respectively. The filter 710 substantially transmits the emanating light from the particles at wavelength $\lambda e$ (or $\lambda e1$ and $\lambda e2$), and substantially blocks the excitation light at wavelengths $\lambda 1$, $\lambda 2$. The resulting transmitted light is shown as light 712b in FIG. 7. The filter 710 may be or comprise an absorptive filter, a reflective filter, a scattering filter, and/or any other suitable type of filter that is effective to separate the light emitted by the particles from the excitation light. If the filter 710 is reflective, the blocked portions of the incident light 712a may be reflected as blocked light 712c.

Figure 8:
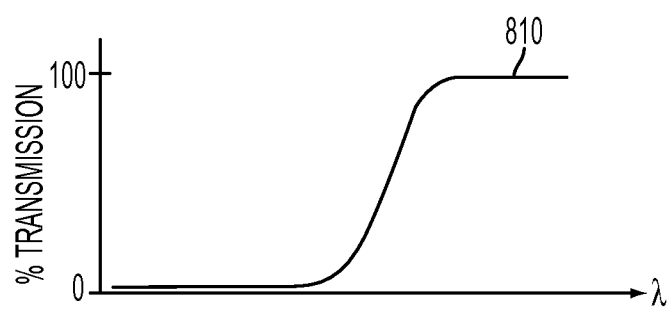
FIG. 8 is a graph of percent transmission versus wavelength for an idealized long pass optical filter.
Figure 9:
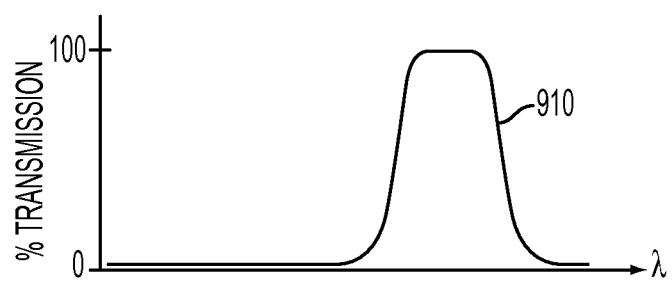
FIG. 9 is a graph of percent transmission versus wavelength for an idealized band pass optical filter.

In most cases, emanating light from a given particle type occurs at an emission wavelength $\lambda e$ that is longer (having a lower photon energy) than that of the excitation light used to excite that particle. FIGS. 8 and 9 are graphs of transmission characteristics of idealized long pass and band pass filters that may accomplish the functions depicted in FIG. 7. In FIG. 8, a transmission function 810 has little or no transmission at relatively short wavelengths, at which excitation light from the light sources may occur. The function 810, however, has a much greater transmission at longer wavelengths, at which light emanating from the particles may occur. In FIG. 9, a transmission function 910 again has little or no transmission at relatively short wavelengths, associated with the excitation light sources, and a much greater transmission over a band of longer wavelengths, associated with the light emanating from the particles. The function 910 then drops to low levels of transmission for wavelengths longer than the pass band, which may be useful in filtering out extraneous light that may otherwise fall on the detector and cause noise in the system.

Figure 10:
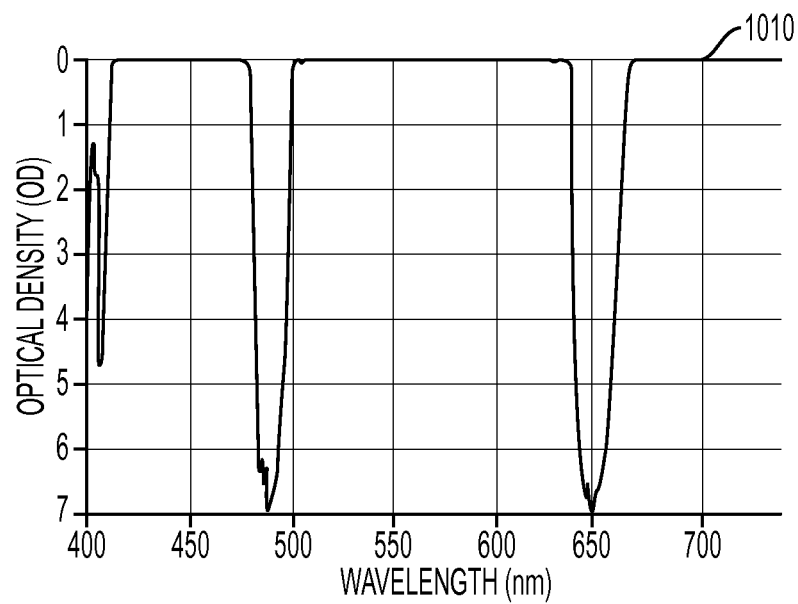
FIGS. 10 and 11 are graphs of optical density (OD) versus wavelength for alternative optical filters that may be used.
Figure 11:
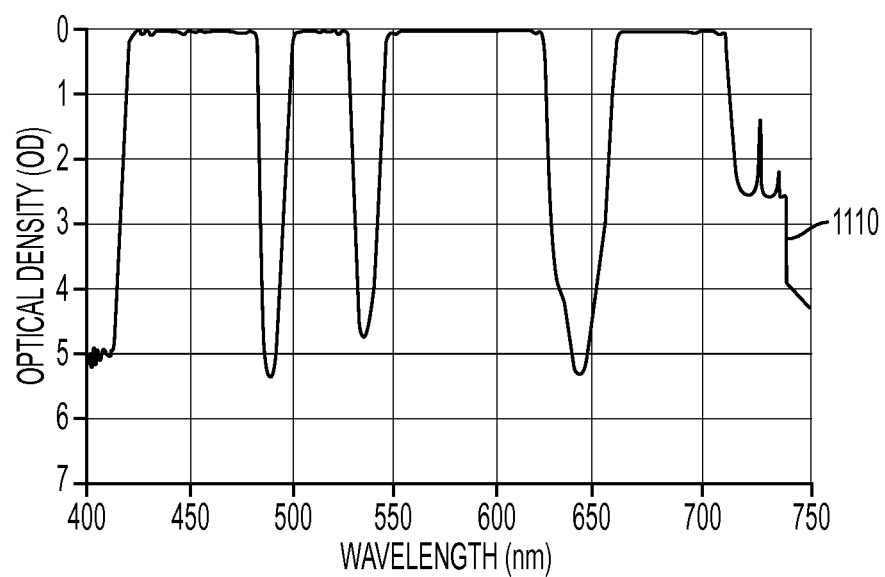

FIGS. 10 and 11 are graphs of actual transmission characteristics of commercially available notch filters that may be used in the disclosed systems. The notch filters are available from Semrock, Inc. These graphs plot optical density (OD) versus wavelength. An optical density of 0 corresponds to a transmission of $1/10^0=1=100\%$, an optical density of 1 corresponds to a transmission of $1/10^1=0.1=10\%$, an optical density of 2 corresponds to a transmission of $1/10^2=0.01=1\%$, and so forth. The transmission functions 1010, 1110 plotted in these figures are characteristic of (multiple) notch filters: they have wide transmission bands and narrow, strong rejection bands. Such filters maximize the spectral regions over which light emission from the particles may occur, by narrowing the rejection bands to only the vicinity of the wavelengths of the excitation sources. Such filters also allow for the use of at least one excitation wavelength that is greater than the wavelength band for emanating light of one of the particle types. For example, the filter of FIG. 10 may be used with a first excitation source operating at $\lambda 1$=485 nm, a second excitation source operating at $\lambda 2$=650 nm, light emission from the first particle type occurring in a range from about 500 to 630 nm, and light emission from the second particle type occurring at wavelengths above about 665 nm. Such a filter may allow for detection of, and differentiation between, frequently used antibody-dye combinations such as Cy3 (or PE) in combination with Cy5.

Figure 12:
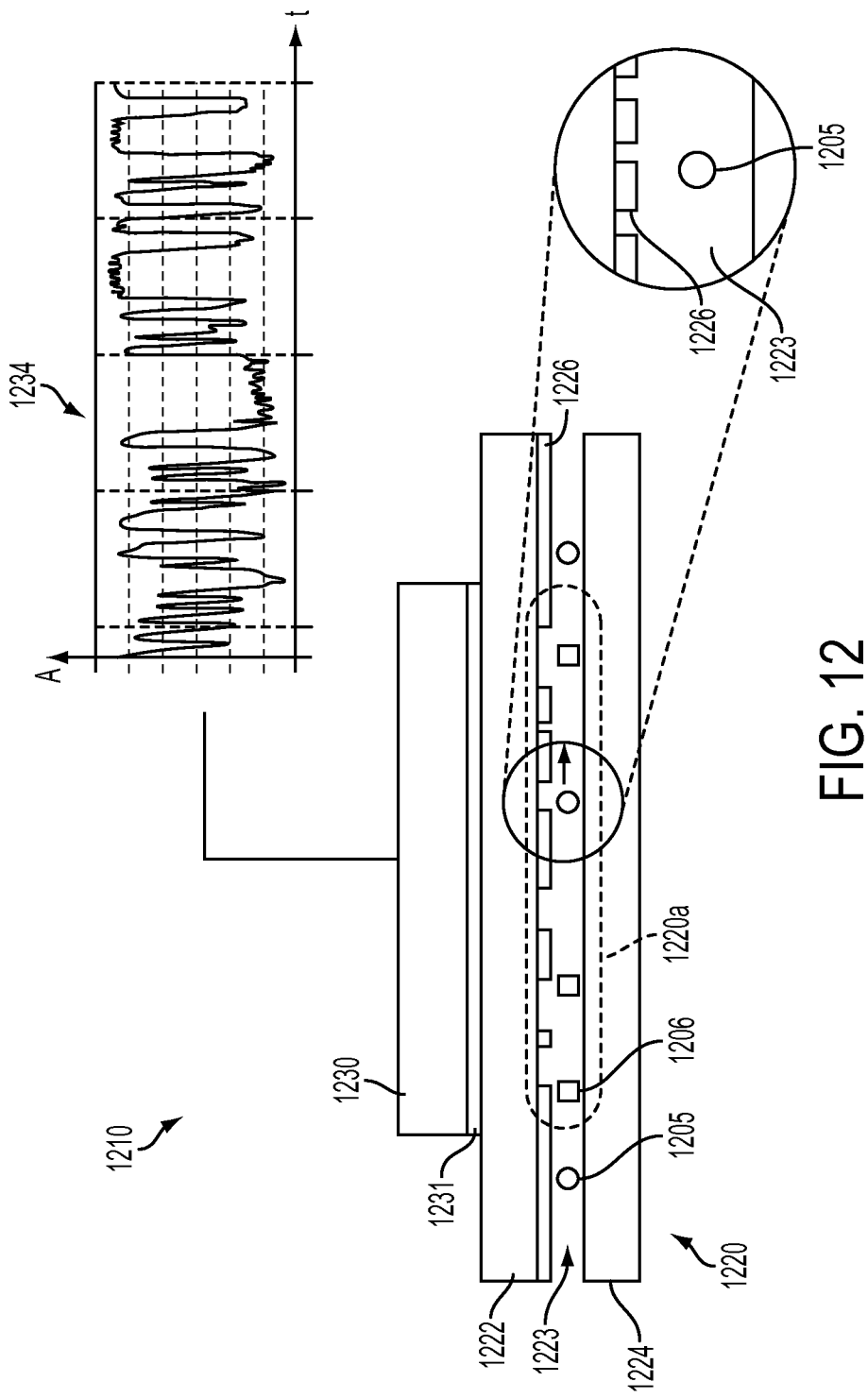
FIG. 12 is a schematic side or sectional view of another sample analyzer.

Another sample analyzer 1210 is shown schematically in FIG. 12. The analyzer 1210 comprises a fluidic device 1220 which may be a fluidic chip. The fluidic device is adapted to receive the sample of interest to be tested, and to cause the sample to flow through a flow channel 1223 formed between confining members 1222, 1224. A syringe, pump, or other suitable device may be used to provide such sample flow. The sample may include first particles 1205 and second particles 1206 having different excitation characteristics as discussed elsewhere herein. A first and second light source (not shown) may be configured to illuminate an excitation region 1220a of the flow channel 1223. The first light source may emit first excitation light that is centered at or peaks at a first wavelength $\lambda 1$, the second light source may emit second excitation light that is centered at or peaks at a second wavelength $\lambda 2$, and the confining member 1222 may be substantially transmissive to both wavelengths $\lambda 1$ and $\lambda 2$. In some cases, one or both light sources may be disposed at a position to the left of the figure, at a position to the right of the figure, at a position above the plane of the figure, and/or and a position below the plane of the figure. The light sources may illuminate substantially the same excitation region 1220a.

The first excitation light is effective to excite light emission from the first particles 1205 (while not substantially exciting light emission from the second particles 1206); the second excitation light is effective to excite light emission from the second particles 1206 (while not substantially exciting light emission from the first particles 1205). Preferably, the first excitation light is modulated at a first frequency $v1$, and the second excitation light is modulated at a second frequency $v2$ different from $v1$, such that the light emanating from the first and second particles 1205, 1206 fluctuates at the same frequencies $v1$, $v2$ respectively.

At least some of the light emanating from the various particles is detected by a photosensitive detector 1230. A first spatial filter 1226 is disposed between the flow channel 1223 and the detector 1230. The detector 1230, and its associated spatial filter 1226 are disposed locally, i.e., at or on the fluidic device 1220. The spatial filter 1226 has a working portion characterized by a sequence of transmissive and non-transmissive regions arranged along the longitudinal direction, which is disposed at or on the confining member 1222 at an edge or boundary of the flow channel 1223. The working portion also corresponds to a detection portion of the flow channel 1223 for purposes of detector 1230. The detector 1230 provides its own detector output, depicted schematically in the figure as signal 1234, which varies in time in accordance with at least: the passage of excited particles through the detection portion of the flow channel 1223; the pattern of transmissive and non-transmissive regions of the spatial filter 1226; and the modulation of the excitation light sources. The detector output 1234 may then be evaluated and analyzed using the various signal analysis techniques discussed herein. An optical emission filter 1231 may be provided for the detector 1230 in order to block at least any residual excitation light that would otherwise fall on the detector, while transmitting light emanating from the particles of interest.

Figure 13:
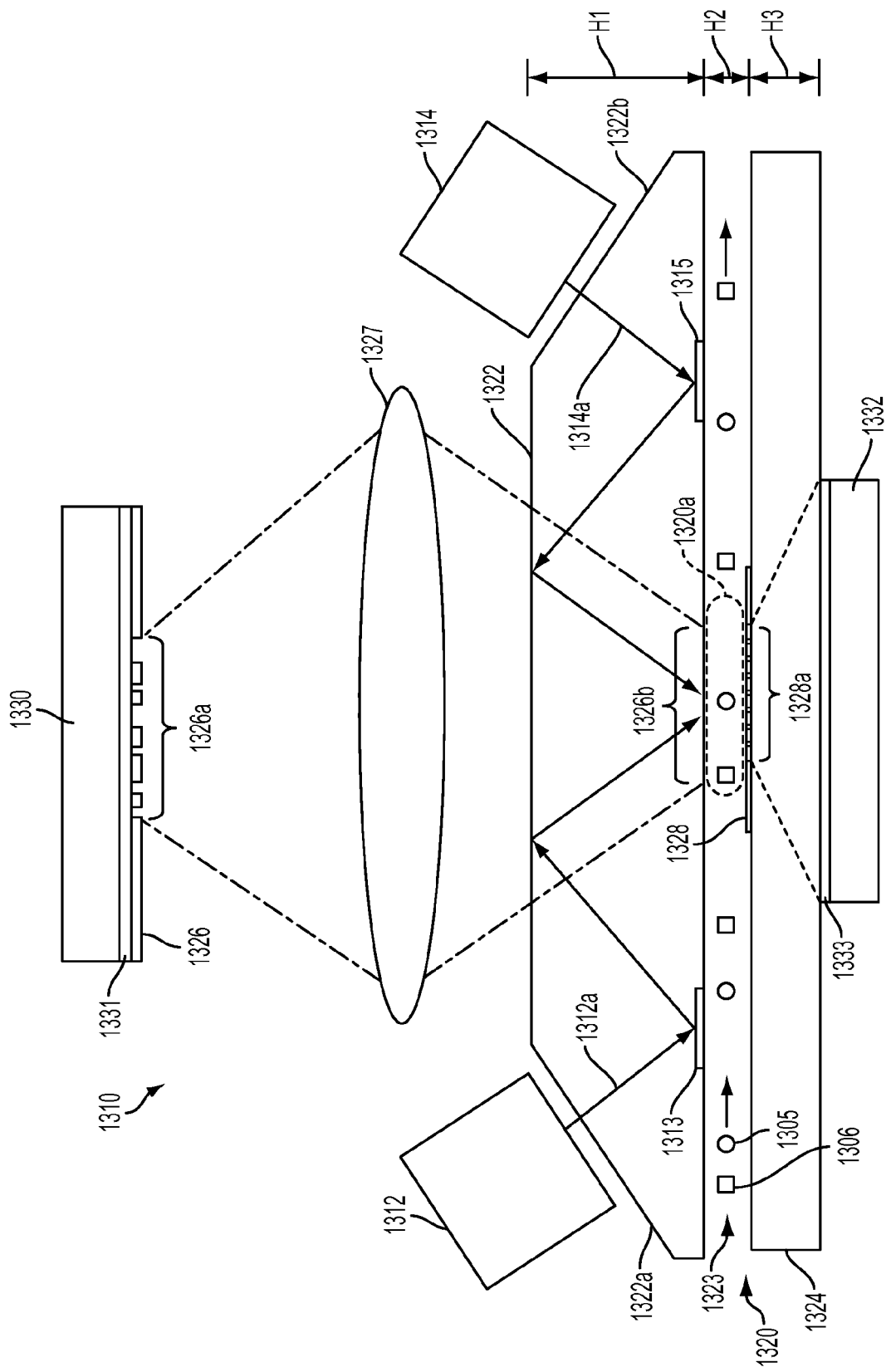
FIG. 13 is a schematic side or sectional view of another sample analyzer.

Another sample analyzer 1310 is shown schematically in FIG. 13. This analyzer, and the other analyzers described herein, may be or comprise a POC flow cytometer. The analyzer 1310 includes a fluidic device 1320 which may be a fluidic chip. The fluidic device is adapted to receive the sample of interest to be tested, and to cause the sample to flow through a flow channel 1323 formed between confining members 1322, 1324. A syringe, pump, or other suitable device may be used to provide such sample flow. The sample may include first particles 1305 and second particles 1306 having different excitation characteristics as discussed elsewhere herein. A first light source 1312 and a second light source 1314 are coupled to respective interfaces 1322a, 1322b of the confining member 1322, the interfaces being angled surfaces of the confining member 1322 to allow excitation light from the light sources to propagate within the confining member 1322 and illuminate an excitation region 1320a of the flow channel 1323. The first light source 1312 may emit first excitation light 1312a that is centered at or peaks at a first wavelength $\lambda 1$, the second light source 1314 may emit second excitation light 1314a that is centered at or peaks at a second wavelength $\lambda 2$, and the confining member 1322 is substantially transmissive to both wavelengths $\lambda 1$ and $\lambda 2$. The light sources 1312, 1314 are preferably solid state devices such as laser diodes or LEDs. In the depicted embodiment, light 1312a is internally reflected by a first mirror 1313 and then internally reflects against an inner boundary surface of confining member 1322 as shown in the figure before illuminating the excitation region 1320a of the flow channel. Light 1314a is similarly internally reflected by a second mirror 1315 and then internally reflects against the inner boundary surface of confining member 1322 before illuminating substantially the same excitation region 1320a. In some cases, one or both of mirrors 1313, 1315 may be omitted and replaced with total internal reflection (TIR) at an air interface, e.g. by providing suitable air gaps (note that the flow channel 1323 can be redirected or reconfigured such that it does not reside in the vicinity of mirrors 1313, 1315).

The first excitation light 1312a is effective to excite light emission from the first particles 1305 (while not substantially exciting light emission from the second particles 1306); the second excitation light 1314a is effective to excite light emission from the second particles 1306 (while not substantially exciting light emission from the first particles 1305). Preferably, the first excitation light 1312a is modulated at a first frequency $v1$, and the second excitation light 1314a is modulated at a second frequency $v2$ different from $v1$, such that the light emanating from the first and second particles 1305, 1306 fluctuates at the same frequencies $v1$, $v2$ respectively.

At least some of the light emanating from the various particles is detected by photosensitive detectors 1330, 1332. Each of these detectors may have its own spatial filter associated with it in order to derive more information from the excited particles. A first spatial filter 1326 is disposed at the detector 1330. A working portion 1326a of the filter 1326, characterized by a sequence of transmissive and non-transmissive regions arranged along the longitudinal direction, is imaged by an optical element 1327 such as one or more suitable lenses and/or mirrors onto a detection portion 1326b of the flow channel 1323. The optical element 1327 may provide magnification, in which case the detection portion 1326b may be smaller or larger than the working portion 1326a. In this configuration, the detector 1330 and the spatial filter 1326 are both remotely disposed relative to the fluidic device 1320. The remote configuration can allow for more convenient repair or replacement of the remotely-located parts, e.g., the detector 1330 and/or the spatial filter 1326. In some cases, for example, the spatial filter 1326 may be removeably mounted to allow for replacement with a different spatial filter having a different pattern of transmissive and non-transmissive regions.

By contrast, the detector 1332, and its associated spatial filter 1328, are not remotely configured but are instead disposed locally, i.e., at or on the fluidic device 1320. This local configuration can allow for a more compact and simpler design than a remote configuration. The spatial filter 1328 has a working portion 1328a, which is disposed at or on the confining member 1324 at an edge or boundary of the flow channel 1323. The working portion 1328a also corresponds to a detection portion of the flow channel 1323 for purposes of detector 1332. The portion 1326b and the portion 1328a may be of the same or nominally the same size, and both may substantially overlap with the excitation region 1320a.

Each of the detectors 1330, 1332 provides its own detector output which varies in time in accordance with at least: the passage of excited particles through the detection portion(s) of the flow channel 1323; the pattern of transmissive and non-transmissive regions of the respective spatial filter; and the modulation of the excitation light sources. Each of these detector outputs may then be evaluated and analyzed independently of each other using the various signal analysis techniques discussed herein. Optical emission filters 1331, 1333 may be provided for the respective detectors 1330, 1332 in order to block at least any residual excitation light that would otherwise fall on the detectors, while transmitting light emanating from at least one of the particle types. In some cases, the filters 1331, 1333 may each transmit emanating light from both the first and second particle types, such that the outputs of each detector 1330, 1332 contain signal contributions from both the first and second particles 1305, 1306. In other cases, at least one of the filters 1331, 1333 may block not only the first and second excitation light but also light that emanates from one of the particle types. For example, filter 1331 may block light emanating from the second particles 1306 but transmit light emanating from the first particles 1305, while the filter 1333 may block light emanating from the first particles 1305 but transmit light emanating from the second particles 1306.

Furthermore, a variety of configurations for the detectors and the spatial filters are also contemplated. For example, analyzer 1310 may be modified to provide: a remote detector 1332 but a local spatial filter 1328; a remote detector 1332 and a remote spatial filter 1328; a remote detector 1330 but a local spatial filter 1326; and a local detector 1330 and a local spatial filter 1326. In some cases, the spatial filter 1326 may have substantially the same arrangement or pattern of transmissive and non-transmissive regions as spatial filter 1328. In other cases, the patterns for these filters may be different. One spatial filter may have a periodic pattern, while the other spatial filter may have a non-periodic pattern. Alternatively, one spatial filter may have a first periodic pattern, and the other spatial filter may have a second periodic pattern different from the first pattern. Alternatively, one spatial filter may have a first non-periodic pattern, and the other spatial filter may have a second non-periodic pattern different from the first pattern. One spatial filter may have a monochromatic pattern, while the other spatial filter may have a polychromatic pattern. Alternatively, both spatial filters may have monochromatic patterns, or both may have polychromatic patterns. Furthermore, the detectors 1330, 1332 may have substantially the same detector characteristics, or they may be different. For example, the detectors 1330, 1332 may both be silicon photodiodes, or they may be photodiodes made of some other detector material, and they may thus have substantially the same spectral responsivity. Alternatively, the detectors 1330, 1332 may be composed of different detector materials (e.g., different semiconductors), and they may thus have substantially different spectral responsivities.

In an exemplary embodiment, the analyzer 1310 may be made in a relatively small format suitable for use in POC applications. In such embodiment, the dimensions H1, H2, and H3 in FIG. 13 may be 2 mm, 25 microns, and 75 to 100 microns, respectively, but these dimensions should not be construed to be limiting. Other details regarding suitable analyzer features may be found in Patent Application Publication U.S. 2010/0201988 (Kiesel et al.).

The reader will understand that the concept shown in FIG. 13 of using two different detector/spatial filter combinations can be extended in a straightforward fashion to more than two such combinations. For example, three, four, or more different detectors and/or detector/spatial filter combinations may be used for a given flow channel and analyzer. Furthermore, two, three, or more modulated laser diodes or other modulated excitation sources may be arranged to illuminate substantially the same excitation region 1320a, for example, by arranging such sources in a ring geometry. Such concepts can also be applied to the other analyzers disclosed herein.

Figure 14:
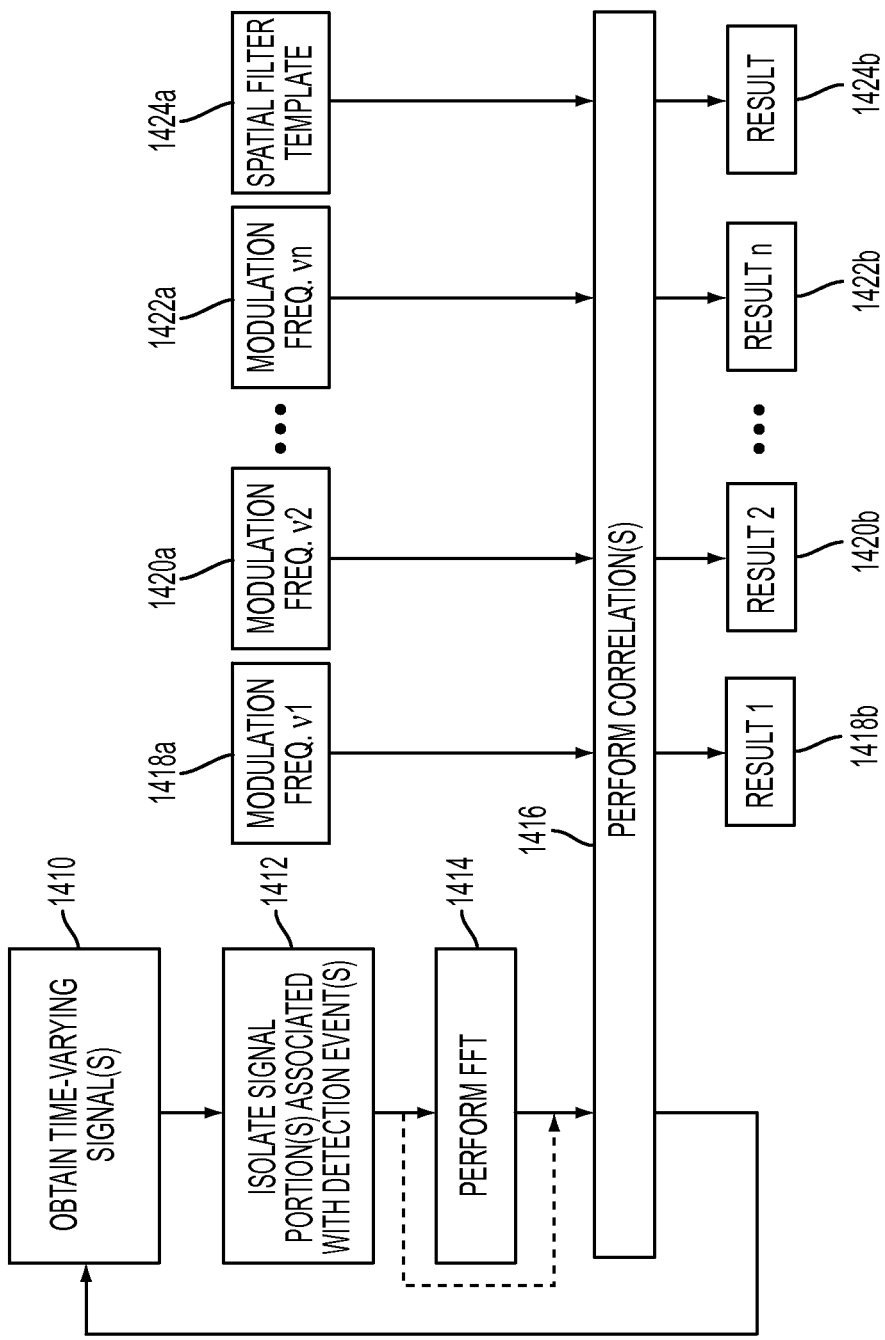
FIG. 14 is a flow diagram depicting a method that can be carried out with the disclosed sample analyzers.

In FIG. 14, we show a flow diagram of a method that may be used in at least some implementations of the disclosed sample analyzers. In box 1410, time-varying signal(s) are obtained from the photosensitive detector(s). (More than one detector may be used on a given analyzer, and each detector may have its own spatial filter, as discussed above.) In box 1412, portions of each time-varying signal associated with detection events are isolated. This procedure may be important when dealing with rare event detection, since in those cases, the detector output may be substantially zero (e.g., at or near the noise floor) for significant periods of time, interrupted by sporadic signal bursts corresponding to a particle of interest passing through the detection portion of the flow channel, which we may refer to as a detection event for such particle. The portion of the time-varying signal corresponding to such a sporadic signal burst may be separated and isolated for individual evaluation and analysis. Alternatively, even in cases involving high particle concentrations, where at least one particle is likely to be present in the detection portion of the flow channel at any given time, the continuous time-varying output signal of the detector may be subdivided into isolated signal portions of manageable size for signal processing purposes. The isolated signal portion may also represent a sliding time window of the continuous detector output, e.g., being constantly updated with the newest raw data points as the oldest raw data points are discarded.

In box 1414, a frequency spectrum of each signal portion is calculated. The frequency spectrum may be calculated using a fast Fourier transform (FFT) technique, or by any other suitable technique. In addition to calculation of the frequency spectrum, some analysis may be carried out. Local maxima or peaks, and/or a dominant peak, in the frequency spectrum may be identified, and their coordinates in amplitude and frequency may be measured and stored. The amplitude of the frequency spectrum may be measured at one or more predetermined frequencies, such as at the modulation frequencies $\nu 1$, $\nu 2$ of the light sources. The measured amplitudes may be compared to each other and/or to one or more threshold values, e.g., so as to distinguish from the noise floor or to distinguish small signal levels from large signal levels. Ratios of the amplitudes may also be calculated.

In box 1416, correlations may be performed on the signal portion of the detector output. For example, correlations between the signal portion and the modulation frequencies, shown in boxes 1418a, 1420a, . . . , 1422a, may be calculated, with the results shown respectively in boxes 1418b, 1420b, . . . , 1422b. Furthermore, the correlation between the signal portion and a template signal, shown in box 1424a, may be calculated to provide a result shown in box 1424*b*. The template signal may be representative of the spatial transmission function of the spatial filter. If the spatial transmission function (and hence also the template signal) is non-periodic, this correlation of the signal portion with the template signal can be used to determine the longitudinal position of the particle in the flow channel.

In some cases, correlations in box 1416 involving the modulation frequencies ν1, ν2, . . . νn can be performed without calculating an entire frequency spectrum as in box 1414. In other cases, calculation of the frequency spectrum in box 1414 may be performed without calculating the correlations in box 1416.

Figure 15:
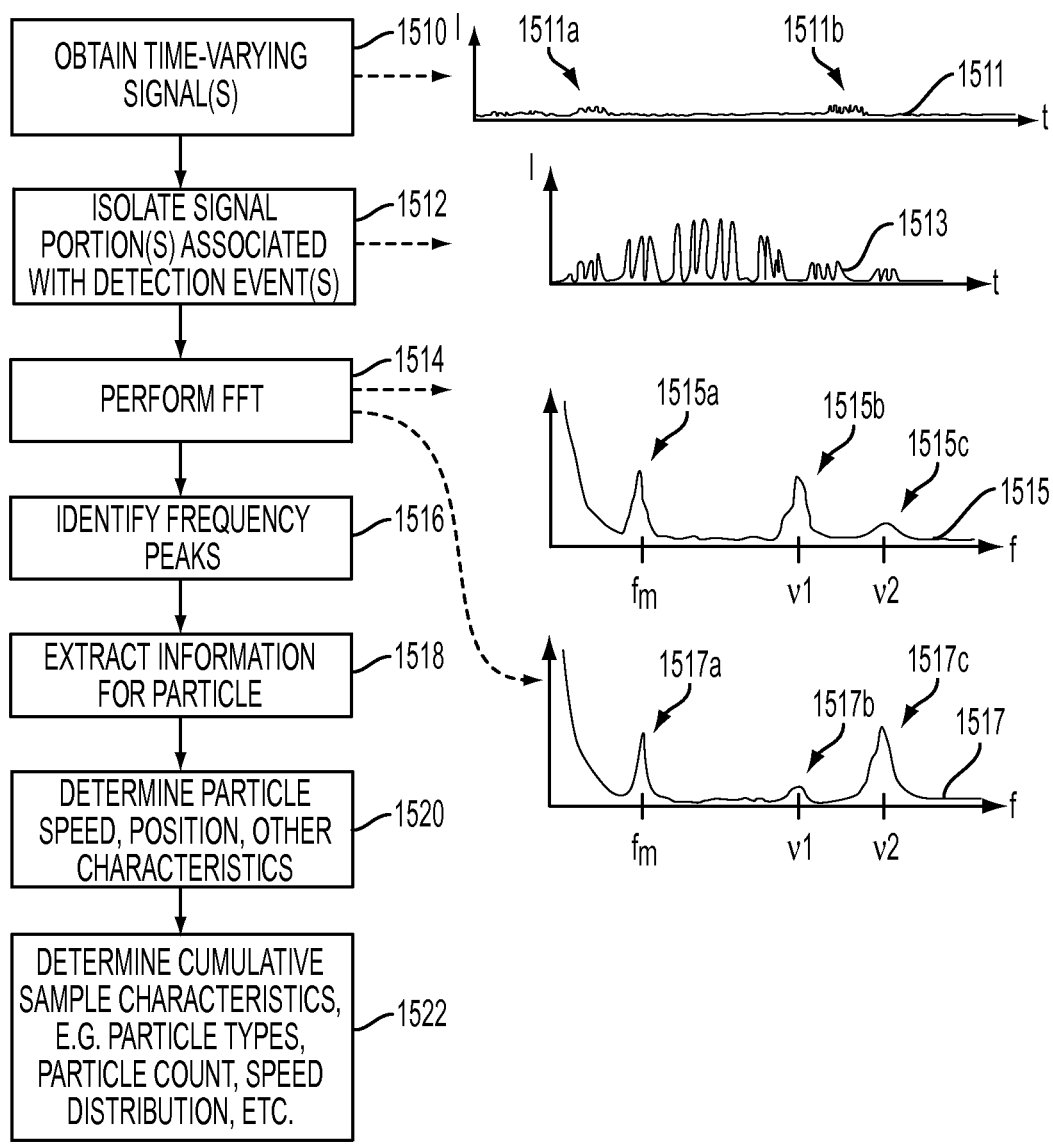
FIGS. 15 and 16 are flow diagrams depicting additional methods that can be carried out with the disclosed analyzers.

In FIG. 15, we show a flow diagram of another method that may be used in at least some implementations of the disclosed sample analyzers. In box 1510, time-varying signal(s) are obtained from the photosensitive detector(s). A possible detector output signal 1511 is shown in a graph of intensity (I) versus time (t), the signal being representative of low particle concentrations (rare event detection) with sporadic signal bursts 1511*a*, 1511*b*. In box 1512, portions of each time-varying signal associated with detection events are isolated. A possible signal portion 1513 associated with one such detection event is shown in a graph of intensity (I) versus time (t).

In box 1514, a frequency spectrum of each signal portion is calculated, e.g., using a fast Fourier transform (FFT) technique or other suitable technique. Two possible outcomes of this procedure are shown as frequency spectrum 1515 and frequency spectrum 1517, each spectrum plotted on a graph of amplitude versus frequency (f). The spectrum 1515 is representative of a signal portion containing information from the first particle, which is excited by the first light source at the modulation frequency ν1. The spectrum 1517 is representative of a signal portion containing information from the second particle, which is excited by the second light source at the different modulation frequency ν2. The spectrum 1515 contains a major frequency component 1515*b* at the frequency ν1 and a major frequency component 1515*a* at the mask frequency $f_m$. The spectrum 1517 contains a major frequency component 1517*c* at the frequency ν2 and a major frequency component 1517*a* at the mask frequency $f_m$. (The peaks at the mask frequency $f_m$ assume the spatial filter has a transmission function that is periodic or substantially periodic. The frequency $f_m$ corresponds to the spatial frequency of the spatial filter multiplied by the speed of the particle.) Minor frequency components or peaks 1515*c*, 1517*b* can also be seen in the respective spectra 1515, 1517. These minor components may be the result of particles that have a non-zero response to the excitation light from each of the light sources. Thus, minor component 1515*c* may be the result of the first particle emanating a relatively small amount of light in response to excitation from the second light source (modulation frequency ν2), and minor component 1517*b* may be the result of the second particle emanating a relatively small amount of light in response to excitation from the first light source (modulation frequency ν1).

In box 1516, additional analysis may be carried out. Local maxima or peaks, and/or a dominant peak, in the frequency spectrum may be identified, and their coordinates in amplitude and frequency may be measured and stored. The amplitude of the frequency spectrum may be measured at one or more predetermined frequencies, such as at the modulation frequencies ν1, ν2 of the light sources. These amplitudes may be compared with each other and/or with other parameters. Ratios of the amplitudes may also be calculated.

In box 1518, information on the particle(s) detected in connection with the particular signal portion is extracted. Such extracted information may include information shown in box 1520. The particle type may be determined by comparing the amplitude of the frequency spectrum at the modulation frequencies ν1, ν2, or by determining whether a peak in the frequency spectrum is present, or is above a given threshold level, at frequency ν1 or frequency ν2. The particle size may be determined by the absolute amplitude of the frequency spectrum at the modulation frequencies ν1, ν2. If the spatial filter is periodic, and even in some cases where it is non-periodic (but where the transmission function has a dominant spatial frequency), the speed of the particle can be determined by identifying another peak in the frequency spectrum, such peak associated with the spatial filter, and measuring the frequency $f_m$ of such peak. If the spatial filter is non-periodic, the position of the particle can be determined by correlating a template signal representative of the transmission function of the spatial filter with the signal portion of the detector output.

In box 1522, cumulative sample information that has been extracted from numerous signal portions of the detector output may be tabulated and compiled. A count of particles may be maintained of the different particle types being identified, and results of particle speed, position, size, and other information may be compiled and analyzed.

Figure 16:
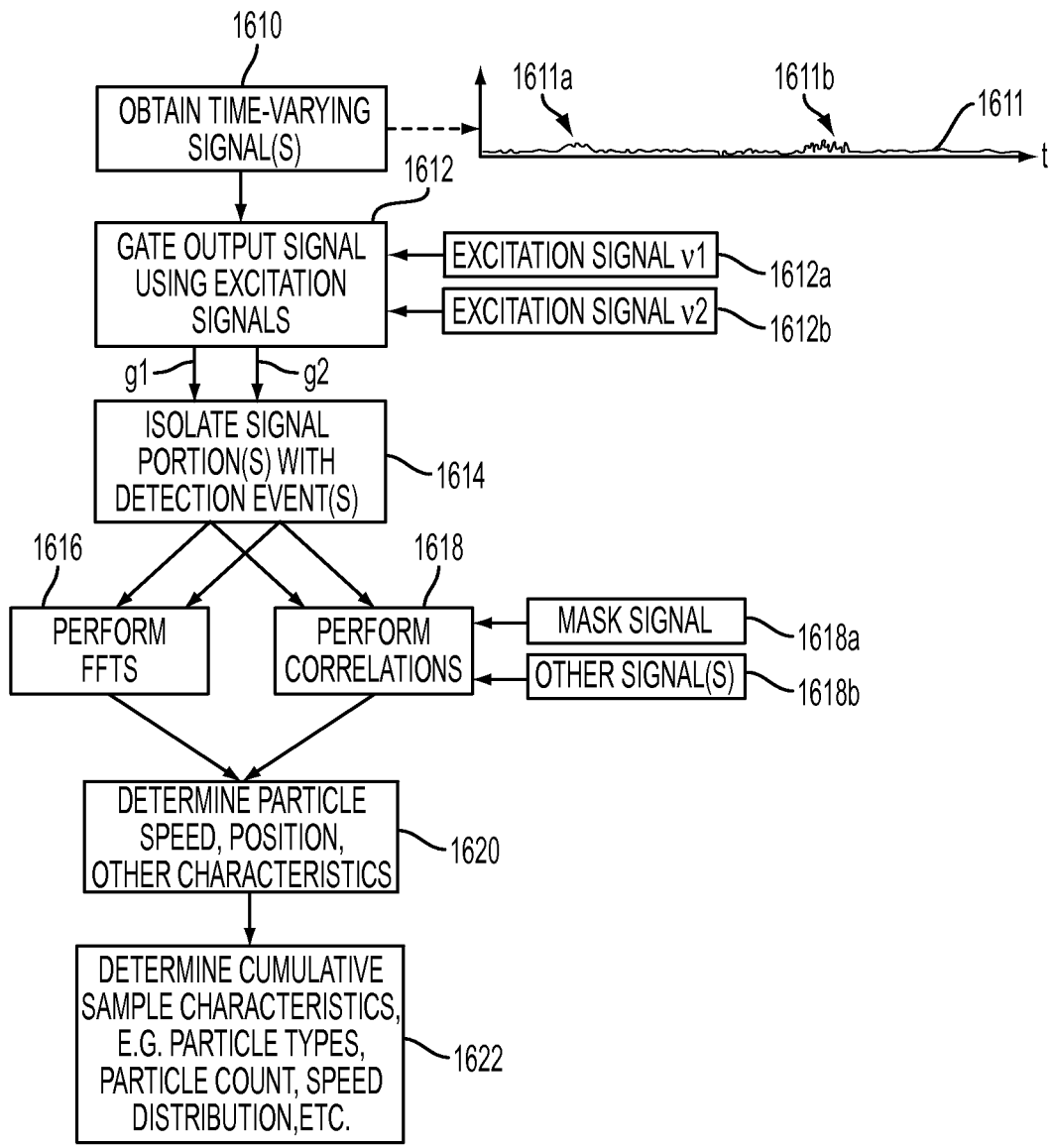

Another method that may be used in at least some implementations of the disclosed sample analyzers is shown in the flow diagram of FIG. 16. In box 1610, time-varying signal(s) are obtained from the photosensitive detector(s). A possible detector output signal 1611 is shown in a graph of intensity (I) versus time (t), the signal being representative of low particle concentrations (rare event detection) with sporadic signal bursts 1611*a*, 1611*b*.

In box 1612, the time-varying output signal from the detector is synchronously gated with the different excitation modulation signals to provide gated time-varying signals g1, g2. Signal g1, for example, may have the same signal amplitude as the original detector output signal during times at which the excitation signal 1612*a* is at a "high" or "on" state, but may have a zero signal amplitude at all other times, when the excitation signal 1612*a* is at a "low" or "off" state. The excitation signal 1612*a* alternates between the "high" or "on" state and the "low" or "off" state at the modulation frequency ν1. Similarly, signal g2 may have the same signal amplitude as the original detector output signal during times at which the excitation signal 1612*b* is at a "high" or "on" state, but may have a zero signal amplitude at all other times, when the excitation signal 1612*b* is at a "low" or "off" state. The excitation signal 1612*b* alternates between the "high" or "on" state and the "low" or "off" state at the modulation frequency ν2. Although only two excitation signals and two gated signals are shown for simplicity in FIG. 16, the reader will understand that the method can be readily extended to larger numbers of excitation signals.

In box 1614, portions of each gated time-varying signal associated with detection events are isolated. In some cases, when a detection event is identified or triggered, a portion of gated signal data corresponding to that detection event can be obtained from each of the gated signals, and analysis can be performed on each such signal portion in connection with the detection event. I.e., analysis can be performed on the signal portion for the first gated signal g1, and analysis can also be performed on the corresponding signal portion for the second gated signal g2. Two arrows are thus shown connecting box 1614 to box 1616, and two arrows are also shown connecting box 1614 to box 1618.

Figure 17:
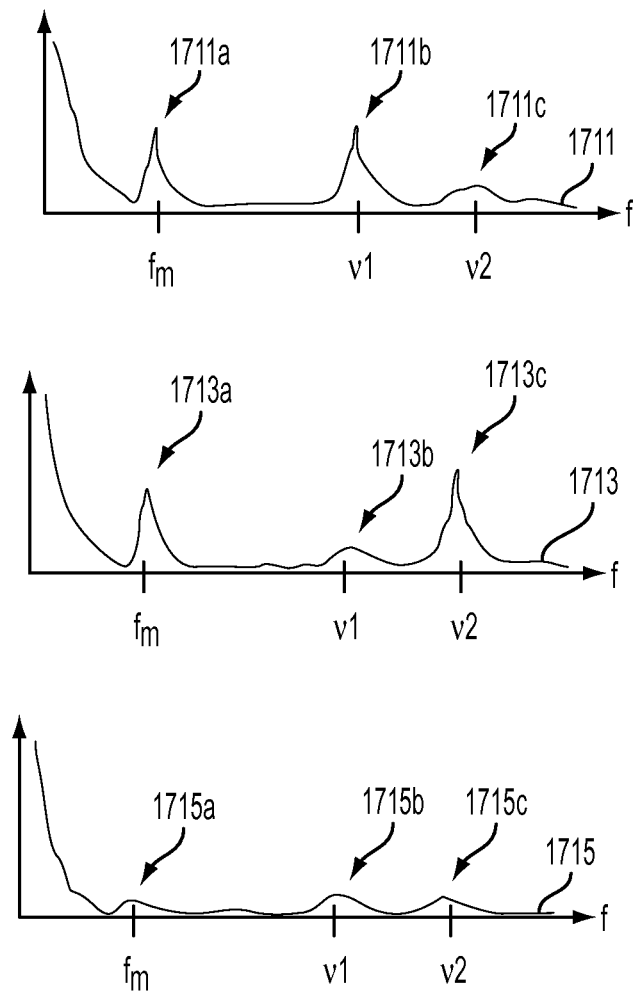
FIG. 17 is a set of hypothetical frequency spectra that may be obtained from the flow diagram of FIG. 16.

In box 1616, a frequency spectrum of each signal portion is calculated, e.g., using a fast Fourier transform (FFT) technique or other suitable technique. Possible outcomes of this procedure are shown as representative frequency spectra in FIG. 17. If the detection event is of the first particle, then spectrum 1711 may fairly represent the spectrum of the signal portion for the first gated signal g1, and spectrum 1715 may fairly represent the spectrum of the signal portion for the second gated signal g2. Since in this scenario the first particle is responsible for the detection event, a major frequency component 1711b is present in the first gated signal at the first modulation frequency v1, and another major frequency component 1711a is present at the mask frequency $f_m$. (A minor frequency component 1711c is shown at the second modulation frequency v2 to reflect the fact that the first particle may be weakly excited by the second excitation source.) Still with respect to this scenario, the signal portion for the second gated signal g2 may exhibit only minor frequency components 1715a, 1715b, 1715c at the respective frequencies $f_m$, v1, v2. The reader will keep in mind that even though this signal portion for the second gated signal g2 corresponds to the detection event for the first particle, the frequency spectrum 1715 may contain only a minor frequency component (1715b), if any, at the first modulation frequency v1, because the frequency spectrum is being calculated for a signal that has been synchronously gated according to the second excitation signal 1612b.

In another scenario, the detection event may be of the second particle. In this case, spectrum 1713 may fairly represent the spectrum of the signal portion for the second gated signal g2, and spectrum 1715 may fairly represent the spectrum of the signal portion for the first gated signal g1. Since in this scenario the second particle is responsible for the detection event, a major frequency component 1713c is present in the second gated signal at the second modulation frequency v2, and another major frequency component 1713a is present at the mask frequency $f_m$. (A minor frequency component 1713b is shown at the first modulation frequency v1 to reflect the fact that the second particle may be weakly excited by the first excitation source.) Still with respect to this scenario, the signal portion for the first gated signal g2 may exhibit only minor frequency components 1715a, 1715b, 1715c at the respective frequencies $f_m$, v1, v2. The reader will keep in mind that even though this signal portion for the first gated signal g1 corresponds to the detection event for the second particle, the frequency spectrum 1715 may contain only a minor frequency component (1715c), if any, at the second modulation frequency v2, because the frequency spectrum is being calculated for a signal that has been synchronously gated according to the first excitation signal 1612a.

In box 1618, correlations may be performed on the signal portions of the first and second gated signals. For example, these signal portions may be correlated with a template signal 1618a representative of the transmission function of the spatial filter or mask. If the transmission function is non-periodic, the correlation results may provide information regarding the longitudinal position of the particle. Correlations may also be calculated with respect to other signals 1618b, such as the modulation signals for the excitation sources.

In box 1620, results from the frequency spectra of box 1616 and from the correlation calculations of box 1618 are evaluated to determine particle information such as particle speed, particle position, particle size (based on the amplitude of the correlation or the amplitude of the frequency spectrum at a given frequency), and other particle characteristics discussed herein.

In box 1622, cumulative sample characteristics may be calculated based on information from all, or at least some, of the particles detected in the sample under test. A count of particles may be maintained of the different particle types being identified, and results of particle speed, position, size, and other information may be compiled and analyzed.

Figure 18:
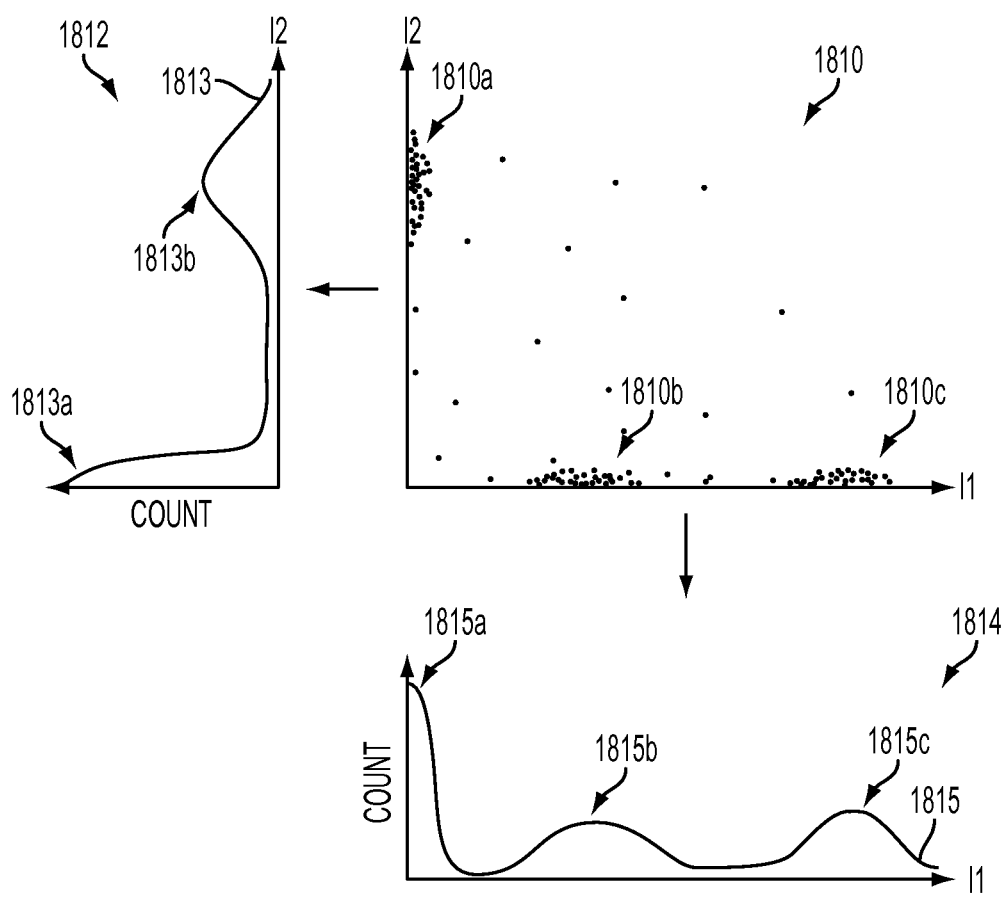
FIG. 18 is a set of graphs that may be obtained using the disclosed analyzers and methods, the graphs containing hypothetical data.

FIG. 18 is a set of graphs that show how data obtained using the disclosed analyzers and methods can be analyzed and evaluated. The main graph 1810 plots the amplitude or magnitude I1 in a first channel against the amplitude or magnitude I2 in a second channel. The I1 and I2 coordinates may be plotted on a linear scale or a logarithmic scale as desired. Each of the hypothetical datapoints in the graph 1810 may represent one of a multitude of detection events measured for a given test sample. The coordinate I1 may be the magnitude of the frequency spectrum at the modulation frequency v1, or the correlation value of the relevant signal portion of the detector output with the modulation frequency v1. The coordinate I2 may be the magnitude of the frequency spectrum at the modulation frequency v2, or the correlation value of the relevant signal portion of the detector output with the template signal expected for the modulation frequency v2.

Inspection of the distribution of hypothetical datapoints in graph 1810 show that the (hypothetical) sample contains three distinct particle types, forming clusters or groups of datapoints 1810a, 1810b, and 1810c. These datapoint groups are located along the I1 and I2 axes. This means that particles that respond (emanate light) to excitation light from the first light source have little or no response to excitation light from the second light source (see groups 1810b, 1810c), and particles that respond to excitation light from the second light source have little or no response to excitation light from the first light source (see group 1810a). This is in keeping with a simple or ideal situation in which particles of a first particle type respond only to excitation light from the first source, and particles of a second particle type respond only to excitation light from the second source. However, we also see now in graph 1810 that distinctions between particle types can also be made based on the strength or magnitude of the response signal. Particles in groups 1810b and 1810c, for example, all respond to excitation light from the first source with little or no response to light from the second source, but particles in the group 1810c provide a stronger signal, whether as a result of having a larger particle size or for other reasons, than particles in the group 1810b. The stronger signal produces a greater magnitude in the I1 coordinate, hence, the group 1810c is shifted along the I1 axis relative to the group 1810b. Boundary conditions can be established to provide three clearly defined regions of the graph corresponding to the groups 1810a, 1810b, 1810c, and the number of datapoints falling within the respective defined regions can provide a count of the three different particle types in the sample. In some cases, any single one of the groups 1810a, 1810b, 1810c may represent not just one particle type but multiple particle types, e.g., a population of small particles and a population of large particles, that yield similar I1 and I2 values. Additional mathematical analysis (e.g., correlation with template functions for small and large particles) can in some cases be used to differentiate such similar particle types or populations also.

Projections of the graph 1810 may also be useful for data analysis. The graph 1812 is a projection along the axis I2. This graph 1812 provides a count of the number of datapoints as a function of the amplitude I2. The resulting curve 1813 exhibits a first peak 1813a, corresponding to the particle groups 1810b and 1810c, and a second peak 1813b, corresponding to the particle group 1810a. The graph 1814 is a projection along the axis I1. This graph 1814 provides a count of the number of datapoints as a function of the amplitude I1. The resulting curve 1815 exhibits a first peak 1815a corresponding to the particle group 1810a, a second peak 1815b corresponding to the particle group 1810*b*, and a third peak 1815*c* corresponding to the particle group 1810*c*. One can see that in the absence of graphs 1810 and 1814, an evaluation of the curve 1813 in graph 1812 may lead the analyzer signal processing circuitry to erroneously conclude that only two particle types, corresponding to peaks 1813*a* and 1813*b*, are present in the sample. On the other hand, an evaluation of the curve 1815 in graph 1814, or an evaluation of the datapoints in the two-dimensional graph 1810, would lead the analyzer signal processing circuitry to correctly conclude that three particle types are present in the sample.

Figure 19:
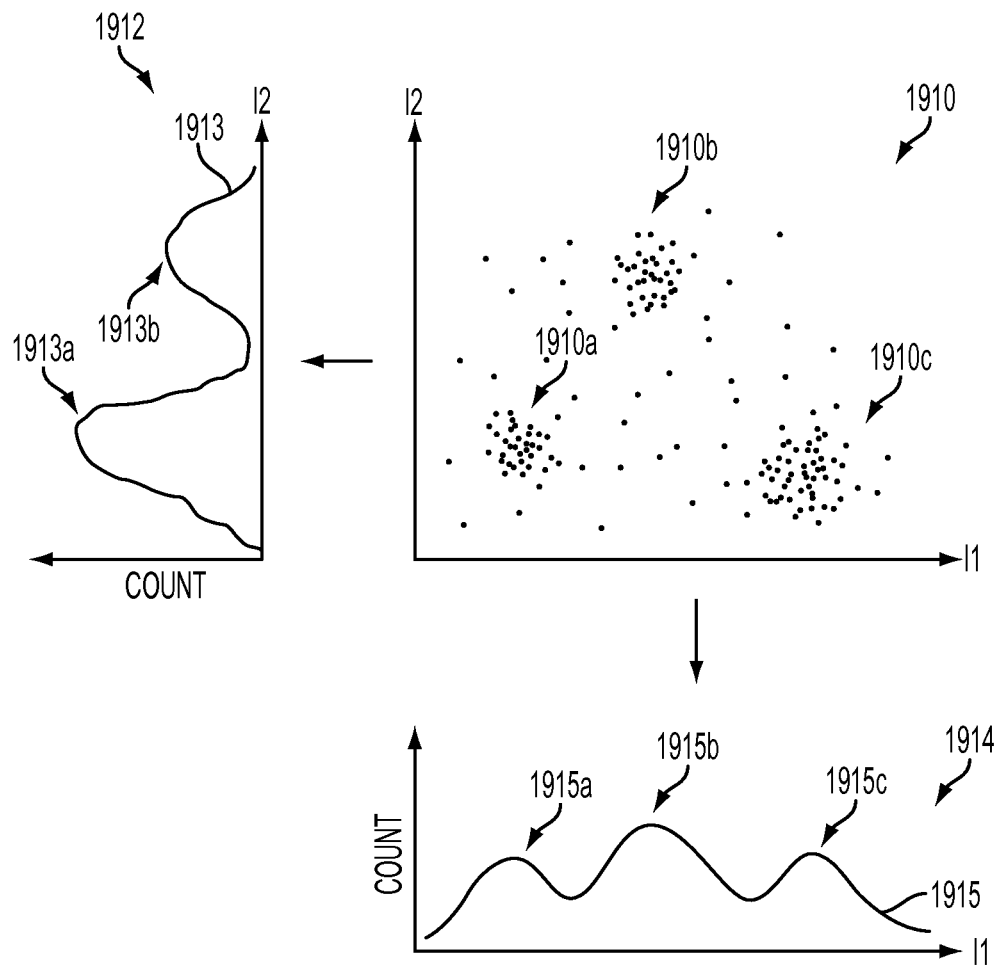
FIG. 19 is a set of graphs similar to those of FIG. 18, but with alternative hypothetical data.

FIG. 19 is a set of graphs similar to those of FIG. 18, but for a different set of hypothetical datapoints. The main graph 1910 plots the amplitude or magnitude I1 in a first channel against the amplitude or magnitude I2 in a second channel. The I1 and I2 coordinates may be plotted on a linear scale or a logarithmic scale as desired. Each of the hypothetical datapoints in the graph 1910 may represent one of a multitude of detection events measured for a given test sample. The coordinate I1 may be the same as or similar to the coordinate I1 in FIG. 18, and the coordinate I2 may be the same as or similar to the coordinate I2 in FIG. 18.

Inspection of the distribution of hypothetical datapoints in graph 1910 show that the (hypothetical) sample contains three distinct particle types, forming clusters or groups of datapoints 1910*a*, 1910*b*, and 1910*c*. Unlike the datapoint groups of FIG. 18, these datapoint groups are located in the coordinate space between the I1 and I2 axes. This means that particles that respond predominantly to excitation light from the first light source also respond to excitation light from the second light source (see group 1910*c*), and particles that respond predominantly to excitation light from the second light source also respond to excitation light from the first light source (see groups 1910*a*, 1910*b*). This is different from the simple or ideal situation in which particles of a first particle type respond only to excitation light from the first source, and particles of a second particle type respond only to excitation light from the second source, but the analyzer signal processing circuitry can nevertheless distinguish between such particles. Just as we saw in connection with FIG. 18, we see again in graph 1910 that the strength or magnitude of the response signal can be used to help make distinctions between particle types. Particles in groups 1910*a* and 1910*b*, for example, all respond to excitation light from the second source to a somewhat greater degree than to light from the first source, but particles in the group 1910*b* provide a stronger signal, whether as a result of having a larger particle size or for other reasons, than particles in the group 1910*a*. The stronger signal produces a greater magnitude in the I1 and I2 coordinates, hence, the group 1910*b* is shifted relative to the group 1910*a*. Boundary conditions can be established to provide three clearly defined regions of the graph corresponding to the groups 1910*a*, 1910*b*, 1910*c*, and the number of datapoints falling within the respective defined regions can provide a count of the three different particle types in the sample.

Projections of the graph 1910 may also be useful for data analysis. The graph 1912 is a projection along the axis I2. This graph 1912 provides a count of the number of datapoints as a function of the amplitude I2. The resulting curve 1913 exhibits a first peak 1913*a*, corresponding to the particle groups 1910*a* and 1910*c*, and a second peak 1913*b*, corresponding to the particle group 1910*b*. The graph 1914 is a projection along the axis I1. This graph 1914 provides a count of the number of datapoints as a function of the amplitude I1. The resulting curve 1915 exhibits a first peak 1915*a* corresponding to the particle group 1910*a*, a second peak 1915*b* corresponding to the particle group 1910*b*, and a third peak 1915*c* corresponding to the particle group 1910*c*. One can see that in the absence of graphs 1910 and 1914, an evaluation of the curve 1913 in graph 1912 may lead the analyzer signal processing circuitry to erroneously conclude that only two particle types, corresponding to peaks 1913*a* and 1913*b*, are present in the sample. On the other hand, an evaluation of the curve 1915 in graph 1914, or an evaluation of the datapoints in the two-dimensional graph 1910, would lead the analyzer signal processing circuitry to correctly conclude that three particle types are present in the sample.

Figure 20:
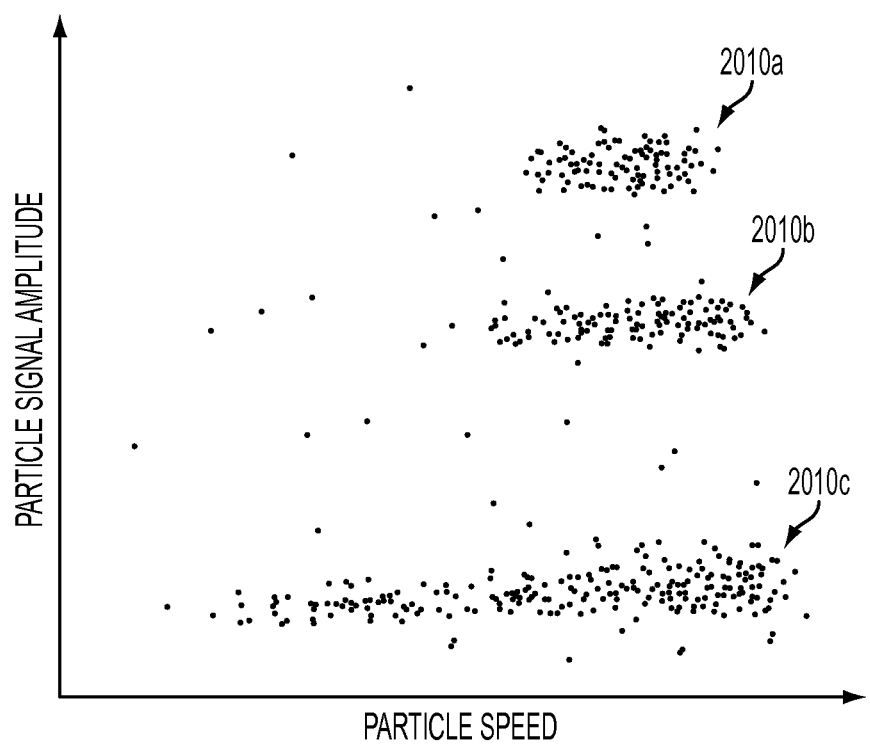
FIG. 20 is a velocity profile graph that plots particle signal amplitude versus particle speed, the graph containing hypothetical data.

Besides signal amplitude in the various channels, the speed of a given particle can also be computed based on a measurement of the mask frequency $f_m$ discussed above. This information can be combined with signal amplitude characteristics to provide further insight regarding particle characteristics of the sample. FIG. 20 is a velocity profile graph that plots particle signal amplitude, such as the coordinate I1 or I2 in FIG. 18 or 19, versus particle speed. The graph again contains hypothetical datapoints representative of all, or at least some, of the particles detected in the sample under test. Inspection of the graph may reveal identifiable groups of particles, e.g. forming clusters or groups of datapoints 2010*a*, 2010*b*, and 2010*c*. Note that the speed information of each particle can also be used to modify the frequency spectrum (e.g. FFT) and/or correlation signals by making adjustments according to particle speed. Since slower particles reside in the detection area for longer times than faster particles, the slower particles tend to provide larger fluorescence signals and higher correlation values than faster particles. The signal processing unit of the measurement system may implement appropriate normalization or other adjustment of the frequency spectrum and/or correlation signals to correct for this effect.

The FFT signal or other frequency component of the detector output signal at the source modulation frequencies v1 and/or v2 can be used as a particle trigger. Since the source modulation frequencies v1, v2 are precisely known, and can be provided as inputs to the signal processing unit, this allows for the use of advanced electronic filtering (such as lock-in techniques and/or digital filtering) to provide extremely sensitive particle detection. Sophisticated FFT analysis and/or correlation techniques can then be used to provide detailed particle discrimination and characterization, for example: ratios of the FFT signal or other frequency components may be used to identify particle type; details in the power (frequency) spectrum or in the value of the measured mask frequency $f_m$ (in the case of a periodic or substantially periodic mask) may be used to determine particle speed; correlations with different specific test/template functions can be used to provide particle size, detailed color information, lifetime of a fluorescence tag, and so forth.

The same measured signal (e.g. a given data string from the detector output signal) can be correlated with multiple different expected signals in order to obtain additional information on the sample, such as details on particle size, by analyzing the signal for missing features or less pronounced features, or weaker modulation of part of the signal. If a patterned color mask is used, multiple correlations with different test functions can reveal very small differences in the emission spectra of different particles. The absolute correlation value, and/or a comparison in correlation values for different particles, may be important in this regard. For example, a signal processing unit may be configured to determine which test function yields the highest correlation value, regardless of the absolute magnitudes of the correlations.

Much of the above disclosure deals with differentiating between only two particle types, but greater numbers of particle types can also be distinguished. Even in systems having only two light sources, modulated at respective frequencies v1 and v2, for example, more than two particle types can be distinguished. In a simple example involving three particle types, one particle type (such as cell tagged with PerCP) may interact with light of the first source at frequency v1, a second particle type (such as a cell tagged with APC) may interact with light of the second source at frequency v2, and a third particle type (such as a cell tagged with a 50:50 mixture of PerCP and APC) may interact (e.g. substantially equally) with both light of the first source at frequency v1 and light of the second source at frequency v2. Those skilled in the art will readily recognize that additional particle types with different dye mixtures can also be used and differentiated. Note that the particle types can be differentiated with high certainty since the ratio of signal strengths at the modulation frequencies v1, v2 can be used. Such ratios are normalized values that tend to cancel out influences due to minor differences in experimental set-up and particle properties.

Much of the above disclosure deals with fluorescent emission from the excited particles. However, other types of emission can also be used, such as resonant Raman scattering. For example, a given particle type may exhibit resonant Raman scattering in response to excitation light from the first light source, or from the second light source, or from both the first and second light sources.

Unless otherwise indicated, all numbers expressing feature sizes, amounts, physical properties, and so forth used in the specification and claims are to be understood as being modified by the term "about". Accordingly, unless indicated to the contrary, the numerical parameters set forth in the specification and claims are approximations that can vary depending on the desired properties sought to be obtained by those skilled in the art utilizing the teachings of the present application.

It will be appreciated that variants of the above-disclosed invention, and other features and functions, or alternatives thereof, may be combined into many other different systems or applications. Various presently unforeseen or unanticipated alternatives, modifications, variations, or improvements therein may be subsequently made by those skilled in the art, and are intended to be encompassed by the following claims.

The invention claimed is:

1. An apparatus for analyzing a sample that may comprise particles of at least a first and second particle type, the apparatus comprising:
    a flow channel through which the sample can pass;
    a first light source adapted to emit first excitation light into a first excitation portion of the flow channel, the first excitation light adapted to stimulate a first light emission from particles of the first particle type;
    a second light source adapted to emit second excitation light into a second excitation portion of the flow channel, the second excitation light adapted to stimulate a second light emission from particles of the second particle type;
    a detector disposed to receive at least a portion of the first and second light emission from the corresponding particles that may be present in the sample in a detection portion of the flow channel, the detection portion overlapping with the first and second excitation portions of the flow channel, the detector adapted to provide a detector output based on the received light emission; and
    a spatial filter having a pattern of variable transmission, the spatial filter being disposed between the detection portion of the flow channel and the detector, the spatial filter further being adapted to transmit light emanating from the particles that may be present in the flow channel by varying amounts as such particles travel along the detection portion of the flow channel;
    wherein the first light source is adapted to emit the first excitation light at a first modulation frequency v1, and the second light source is adapted to emit the second excitation light at a second modulation frequency v2 different from v1 and the first and second modulation frequencies are each faster than a modulation associated with the variable transmission of the spatial filter.

2. The apparatus of claim 1, wherein the first and second excitation portions of the flow channel substantially overlap with each other and with the detection portion of the flow channel, and wherein the spatial filter spans the detection portion.

3. The apparatus of claim 1, further comprising:
    a controller coupled to the first and second light sources, the controller adapted to modulate the first and second light sources at the modulation frequencies v1, v2 respectively.

4. The apparatus of claim 1, wherein the first excitation light has a first peak wavelength, and the second excitation light has a second peak wavelength different from the first peak wavelength.

5. The apparatus of claim 1, wherein the first excitation light is adapted to stimulate little or no light emission from particles of the second type, and the second excitation light is adapted to stimulate little or no light emission from particles of the first type.

6. The apparatus of claim 1, wherein the first light emission comprises fluorescence emitted by particles of the first particle type when exposed to the first excitation light, the apparatus further comprising:
    an optical filter disposed between the detector and the flow channel, the optical filter adapted to preferentially transmit the first light emission and to preferentially block the first excitation light.

7. The apparatus of claim 6, wherein the second light emission comprises fluorescence emitted by particles of the second particle type when exposed to the second excitation light, and wherein the optical filter is also adapted to preferentially transmit the second light emission and to preferentially block the second excitation light.

8. The apparatus of claim 1, further comprising:
    a signal processing unit coupled to the detector to receive the detector output, wherein the signal processing unit provides a system output based on the detector output, the system output providing a first measure of the particles of the first particle type in the sample and a second measure of the particles of the second particle type in the sample.

9. An apparatus for analyzing a sample that may comprise particles of at least a first and second particle type, the apparatus comprising:
    a flow channel through which the sample can pass;
    a first light source adapted to emit first excitation light into a first excitation portion of the flow channel, the first excitation light adapted to stimulate a first light emission from particles of the first particle type and to stimulate little or no light emission from particles of the second type;
    a second light source adapted to emit second excitation light into a second excitation portion of the flow channel, the second excitation light adapted to stimulate a second light emission from particles of the second particle type and to stimulate little or no light emission from particles of the first type;

a detector disposed to receive the first and second light emission from the corresponding particles that may be present in the sample in a detection portion of the flow channel, the detection portion overlapping with the first and second excitation portions of the flow channel, the detector adapted to provide a detector output based on the received light emission;

an optical filter disposed between the detector and the flow channel, the optical filter adapted to preferentially transmit the first and second light emission and to preferentially block the first and second excitation light;

a spatial filter having a pattern of variable transmission, the spatial filter being disposed between the detection portion of the flow channel and the detector, the spatial filter further being adapted to transmit light emanating from the particles that may be present in the flow channel by varying amounts as such particles travel along the detection portion of the flow channel;

a controller coupled to the first and second light sources, the controller adapted to modulate the first light source at a first modulation frequency $v1$, the controller also adapted to modulate the second light source at a second modulation frequency $v2$ different from $v1$; and a signal processing unit coupled to the detector to receive the detector output, wherein the signal processing unit provides a system output based on the detector output, the system output providing a first measure of the particles of the first particle type in the sample and a second measure of the particles of the second particle type in the sample;

wherein the first and second modulation frequencies are each faster than a modulation associated with the variable transmission of the spatial filter.

10. A method for analyzing a sample that may comprise particles of at least a first and second particle type, the method comprising:

passing the sample through a flow channel;

illuminating the sample in a first excitation portion of the flow channel with first excitation light from a first light source while the sample flows through the flow channel, the first excitation light adapted to stimulate a first light emission from particles of the first particle type;

illuminating the sample in a second excitation portion of the flow channel with second excitation light from a second light source while the sample flows through the flow channel, the second excitation light adapted to stimulate a second light emission from particles of the second particle type, the first and second excitation portions of the flow channel overlap with each other and with a detection portion of the flow channel; and detecting at least a portion of the first and second light emission with a detector adapted to provide a detector output based on the received light emission;

transmitting light emanating from the particles that may be present in the flow channel by varying amounts as such particles travel along the detection portion of the flow channel using a spatial filter having a pattern of variable transmission, the spatial filter being disposed between the detection portion of the flow channel and the detector wherein the illuminating is carried out such that the first excitation light is modulated at a first modulation frequency $v1$, and the second excitation light is modulated at a second modulation frequency $v2$ different from $v1$, and the first and second modulation frequencies are each faster than a modulation associated with the variable transmission of the spatial filter.

11. The method of claim 10, wherein the first and second excitation portions of the flow channel overlap with each other and with a detection portion of the flow channel, the method further comprising:

spatially modulating light emitted from particles in the detection portion of the flow channel, such that the first and second light emission is detected by the detector with a third modulation frequency different from the first and second modulation frequencies, the third modulation frequency being based on a flow rate of the sample through the flow channel.

12. The method of claim 11, wherein the spatially modulating includes providing a mask between the detection portion of the flow channel and the detector.

13. The method of claim 12, wherein the spatially modulating further includes imaging the mask onto the detection portion of the flow channel.

14. The method of claim 10, wherein the modulation of the first excitation light is periodic, and the modulation of the second excitation light is periodic.

15. The method of claim 11, wherein the modulation of the first excitation light is periodic, the modulation of the second excitation light is periodic, and the spatial modulation of the light emitted from particles in the detection portion of the flow channel is periodic.

16. The method of claim 10, wherein the first light emission has a first intrinsic response time and an associated first intrinsic frequency, and wherein the first modulation frequency is less than the first intrinsic frequency.

17. The method of claim 10, wherein the second light emission has a second intrinsic response time and an associated second intrinsic frequency, and wherein the second modulation frequency is less than the second intrinsic frequency.

18. The method of claim 10, further comprising:

performing a frequency analysis of the detector output, the frequency analysis including identifying one or more peaks in a frequency spectrum of the detector output.

* * * * *

UNITED STATES PATENT AND TRADEMARK OFFICE
CERTIFICATE OF CORRECTION

PATENT NO. : 9,029,800 B2  
APPLICATION NO. : 13/206436  
DATED : May 12, 2015  
INVENTOR(S) : Kiesel et al.

Page 1 of 1

It is certified that error appears in the above-identified patent and that said Letters Patent is hereby corrected as shown below:

IN THE SPECIFICATION:
At column 1, line 5, please insert the following section header and paragraph:

--STATEMENT REGARDING FEDERALLY SPONSORED RESEARCH AND DEVELOPMENT
This invention was made with government support under contract number NIH 1R21EB011662-01 (3697), awarded by the National Institute of Health (NIH). The U.S. Government has certain rights in this invention.--

Signed and Sealed this
Third Day of May, 2016

Michelle K. Lee
*Director of the United States Patent and Trademark Office*